(12) United States Patent
Weiner et al.

(10) Patent No.: US 9,677,072 B2
(45) Date of Patent: Jun. 13, 2017

(54) METHODS OF INHIBITING PROLIFERATION OF ESTROGEN-INDEPENDENT CANCER CELLS

(75) Inventors: Louis M. Weiner, Washington, DC (US); Rochelle E. Nasto, Washington, DC (US); Robert Clarke, Washington, DC (US); Erica Golemis, Philadelphia, PA (US); Ilya Serebriiskii, Rockledge, PA (US)

(73) Assignee: Georgetown University, Washington, DC (US)

( * ) Notice: Subject to any disclaimer, the term of this patent is extended or adjusted under 35 U.S.C. 154(b) by 0 days.

(21) Appl. No.: 14/344,773

(22) PCT Filed: Sep. 14, 2012

(86) PCT No.: PCT/US2012/055485
§ 371 (c)(1),
(2), (4) Date: Jul. 28, 2015

(87) PCT Pub. No.: WO2013/040393
PCT Pub. Date: Mar. 21, 2013

(65) Prior Publication Data
US 2015/0353928 A1   Dec. 10, 2015

Related U.S. Application Data

(60) Provisional application No. 61/534,716, filed on Sep. 14, 2011.

(51) Int. Cl.
*C12N 15/11* (2006.01)
*C12N 15/113* (2010.01)

(52) U.S. Cl.
CPC ........ *C12N 15/113* (2013.01); *C12N 2310/14* (2013.01); *C12N 2320/11* (2013.01)

(58) Field of Classification Search
None
See application file for complete search history.

(56) References Cited

U.S. PATENT DOCUMENTS

2004/0086504 A1   5/2004   Sampath et al.
2006/0147478 A1   7/2006   Terrett
2008/0003567 A1   1/2008   Rodriguez et al.

FOREIGN PATENT DOCUMENTS

EP   2 177 615 A1   4/2010

OTHER PUBLICATIONS

Yoshida et al., Mice lacking a transcriptional corepressor Tob are predisposed to cancer, 2003, Genes & Development, vol. 17, pp. 1201-1206.*
O'Malley et al., TOB suppresses breast cancer tumorigenesis, 2009, International Journal of Cancer, vol. 125, pp. 1805-1813.*
Kundu et al., Tob1 induces apoptosis and inhibits proliferation, migration and invasion of gastric cancer cells by activating Smad4 and inhibiting beta-catenin signaling, 2012, International Journal of Oncology, vol. 41, pp. 839-848.*
Ogami et al., Antiproliferative protein Tob directly regulates c-myc proto-oncogene expression through cytoplasmic polyadenylation element-binding protein CPEB, 2014, Oncogene, vol. 33, pp. 55-64.*
Kuske et al., Endocrine therapy resistance can be associated with high estrogen receptor alpha (ERalpha) expression and reduced ERalpha phosphorylation in breast cancer models, 2006, Endocrine-Related Cancer, vol. 13, pp. 1121-1133.*
Lee et al., Gene expression profiling of murine hepatic steatosis induced by tamoxifen, 2010, Toxicology Letters, 199:416-424.*
McDonnell et al., Development of tissue-specific estrogen receptor modulators, 1995, Organ-Selective Actions of Steroid Hormones, pp. 1-28.*
Lilling et al., Differential sensitivity of MCF-7 and LCC2 cells, to multiple growth inhibitory agents: possible relation to high bcl-2/bax ratio?, 2000, Cancer Letters, vol. 161, pp. 27-34.*
Fancillui et al., The interacting RNA polymerase II subunits, hRPB11 and hRPB3, are coordinately expressed in adult human tissues and down-regulated by doxorubicin, 1998, FEBS Letters, vol. 427, pp. 236-240.*
Riggs et al., Decreased chicken ovalbumin upstream promoter transcription factor II expression in tamoxifen-resistant breast cancer cells, 2006, Cancer Research, vol. 66, pp. 10188-10198.*
Le Dily et al., COUP-TFI modulates estrogen signaling and influences proliferation, survival and migration of breast cancer cells, 2008, Breast Cancer Research and Treatment, vol. 110, pp. 69-83.*
Fan et al., Diverse gene expression and DNA methylation profiles correlate with differential adaptation of breast cancer cells to the antiestrogens tamoxifen and fulvestrant, 2006, Cancer Research, vol. 66, pp. 11954-11966.*
Ishiguro et al., Two large subunits of the fission yeast RNA polymerase II provide platforms for the assembly of small subunits, 1998, JMB, vol. 279, pp. 703-712.*
International Patent Application No. PCT/US2012/055485: International Search Report mailed Feb. 27, 2013.

* cited by examiner

*Primary Examiner* — Dana Shin
(74) *Attorney, Agent, or Firm* — Morgan, Lewis & Bockius LLP

(57) ABSTRACT

The invention relates to methods of inhibiting the growth or proliferation of a cell, the method comprising reducing the expression or activity of at least one gene in the cell selected from the group consisting of BLOC1S1, CDC2L1, CNOT1, DDX54, EIF3I, FANCG, FBP1, IER2, KIF1A, LCK, NR2F1, PNRC1, POLR2A, POLR2B, POLR2C, PRPF6, PSMB4, PSMC5, PSMD1, RPS2, SCNN1A, SF3A3, TAF2, TOB1 and TSC22D4.

3 Claims, 24 Drawing Sheets

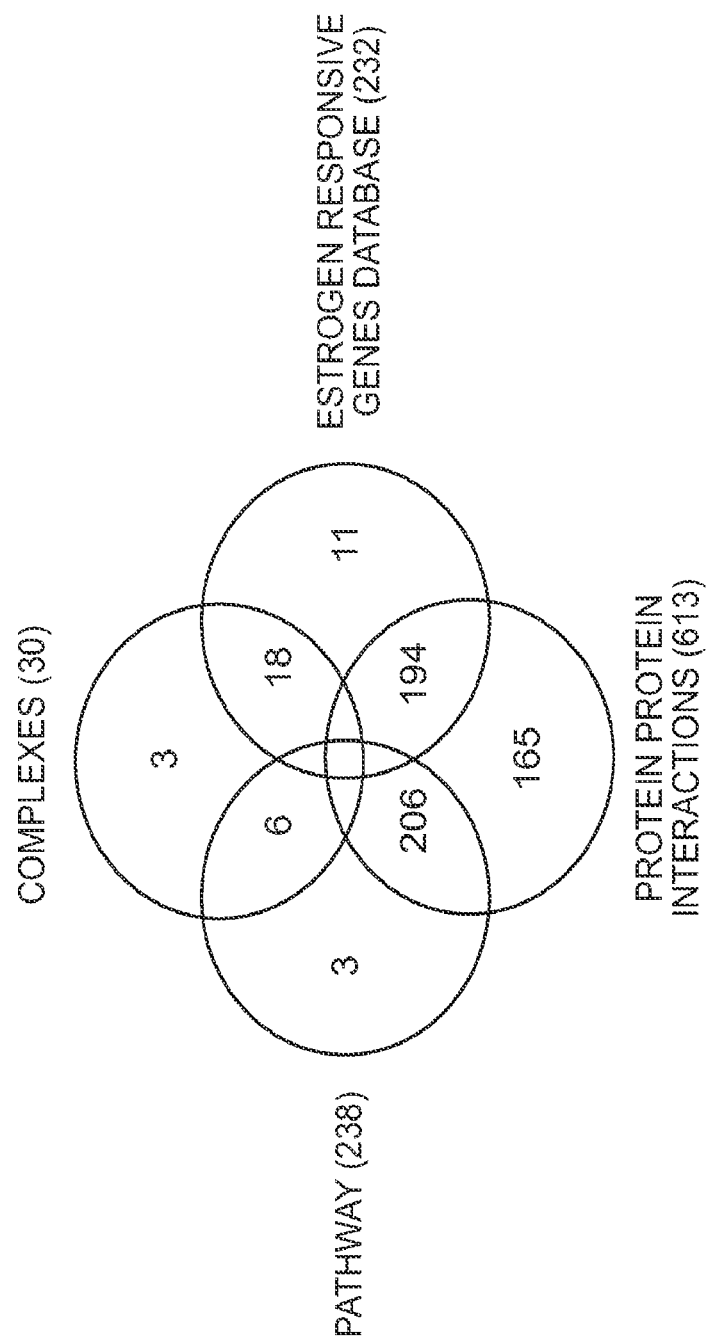

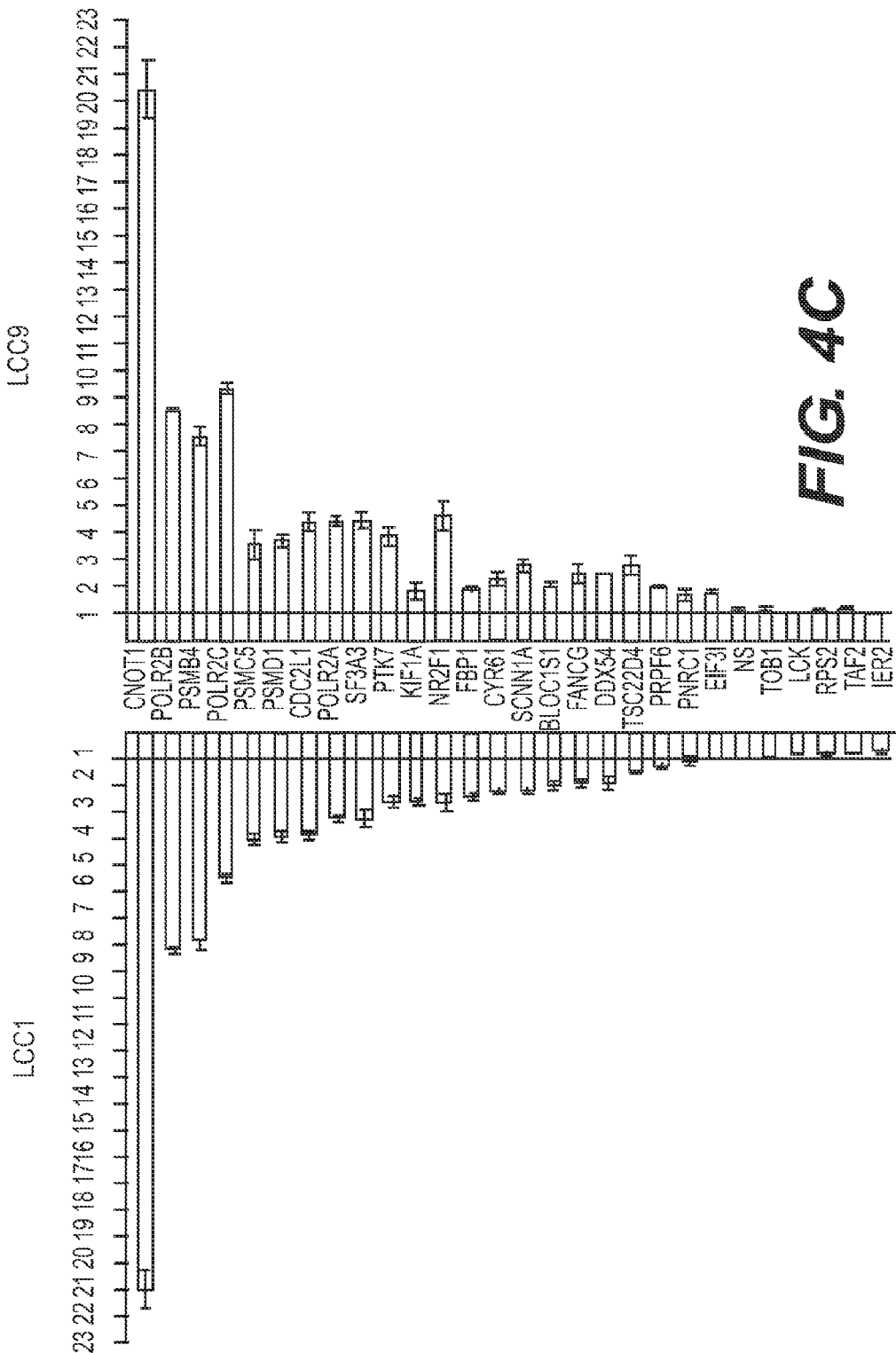

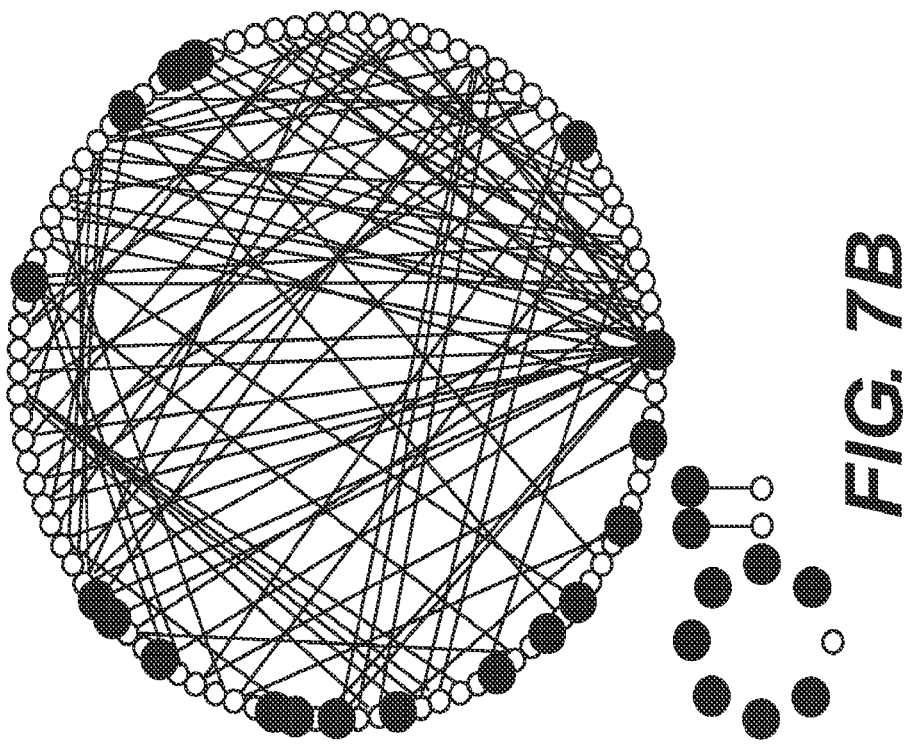

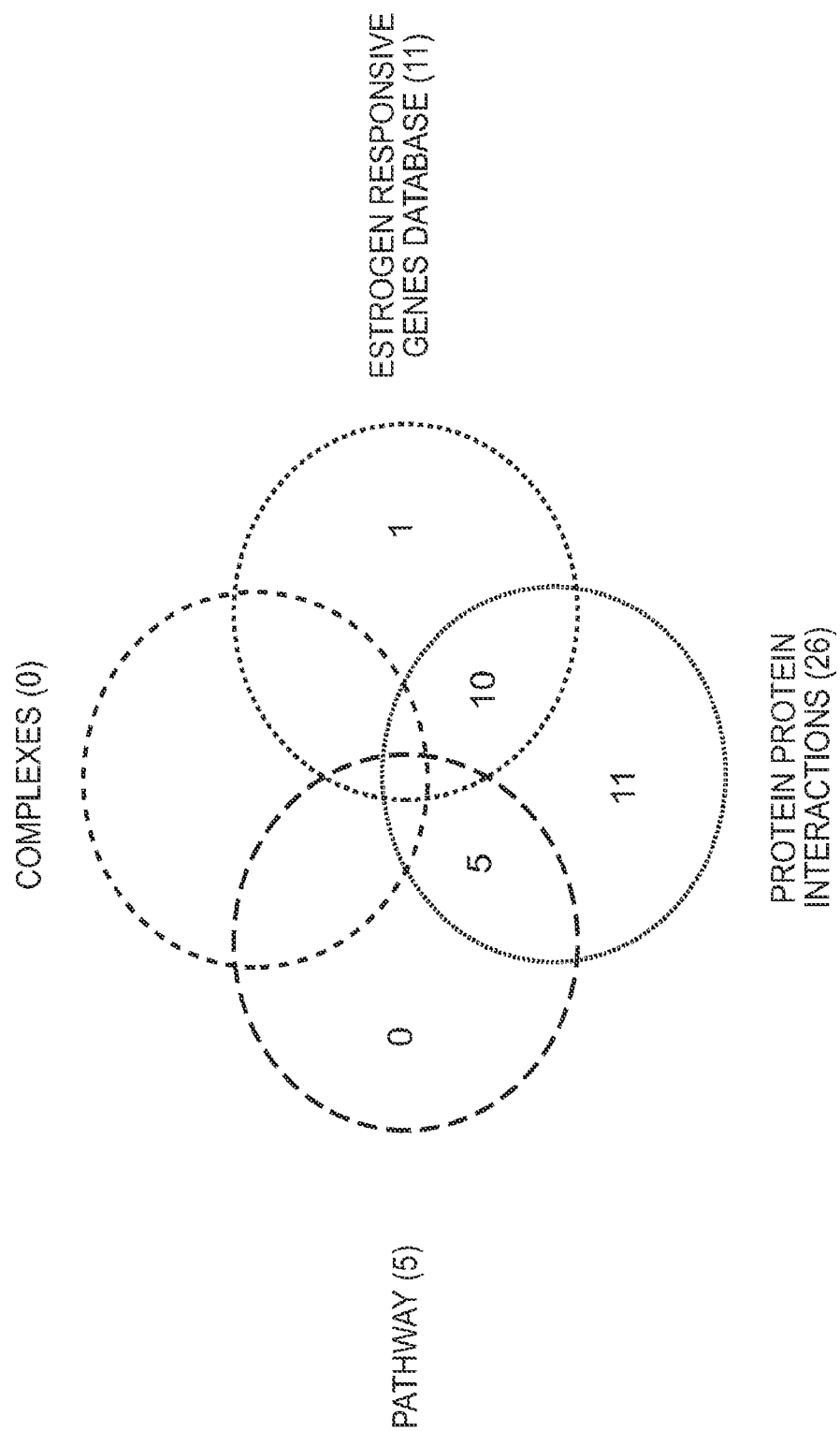

METHODS OF INHIBITING PROLIFERATION OF ESTROGEN-INDEPENDENT CANCER CELLS

CROSS-REFERENCE TO RELATED APPLICATIONS

This application claims priority to U.S. Provisional Application No. 61/534,716, filed 14 Sep. 2011, which is incorporated by reference.

STATEMENT REGARDING FEDERALLY SPONSORED RESEARCH OR DEVELOPMENT

Part of the work performed during development of this invention utilized U.S. Government funds under National Cancer Institute (NCI) Grant No. CA149147-01. The U.S. Government has certain rights in this invention.

SUMMARY OF THE INVENTION

The invention relates to methods of inhibiting the growth or proliferation of a cell, the method comprising reducing the expression or activity of at least one gene in the cell selected from the group consisting of BLOC1S1, CDC2L1, CNOT1, CYR61, DDX54, EIF3I, FANCG, FBP1, IER2, KIF1A, LCK, NR2F1, PNRC1, POLR2A, POLR2B, POLR2C, PRPF6, PSMB4, PSMC5, PSMD1, PTK7, RPS2, SCNN1A, SF3A3, TAF2, TOB1, TSC22D4.

DETAILED DESCRIPTION OF THE INVENTION

Estrogen-independent growth and subsequent resistance to endocrine therapies pose significant challenges to the effective treatment of estrogen receptor (ER) positive breast cancers. Metastatic estrogen receptor positive (ER+) cells typically become estrogen-independent and subsequently resistant to anti-estrogen therapies. The inventors have discovered that changes in the action of proteins interacting with core components of the estrogen response are responsible for both survival and drug resistance, and that inhibition of these proteins may modulate response to endocrine therapies. To test this idea, a network of 631 genes was established using ERα (ESR1), ERβ (ESR2), estrogen related receptors α (ESRRA) and γ (ESRRG), and aromatase (CYP19A1) as seed genes. Next, a set of bioinformatic resources including protein-protein interactions (PPIs), protein complexes, canonical pathways and estrogen responsive genes, was used to generate candidates for inclusion in this network.

An siRNA library was developed from these 631 genes and used to screen a series of breast cancer cell lines for survival following the knockdown of targeted gene expression. Cells used in the assay included MCF7 cells (estrogen dependent/fulvestrant sensitive/tamoxifen sensitive), MCF7/LCC1 cells (estrogen independent/fulvestrant sensitive/tamoxifen sensitive) and MCF7/LCC9 cells (estrogen independent/fulvestrant resistant/tamoxifen cross-resistant) as models with differing estrogen dependence and drug resistance profiles for these initial experiments. The targeted knockdown of 189 genes in this network significantly reduced the viability of MCF7/LCC1 cells. 27 of these genes also are essential for the survival of LCC9 cells. This observation is not limited to the MCF7 cell lineage. The knockdown of most of the 27-genes set described above also significantly reduces the viability of another estrogen independent breast cancer cell line, T47Dco. The targeted inhibition of expression of many of these 27 essential genes induces apoptosis in both LCC1 and LCC9 cells, including genes in the RNA II polymerase and proteasome gene families. These findings have identified potential drug targets for the development of novel strategies for the treatment of estrogen-independent breast cancer and will contribute to the development of new mathematical and computational models that can explain the mechanisms of endocrine resistance.

Figure 1A:
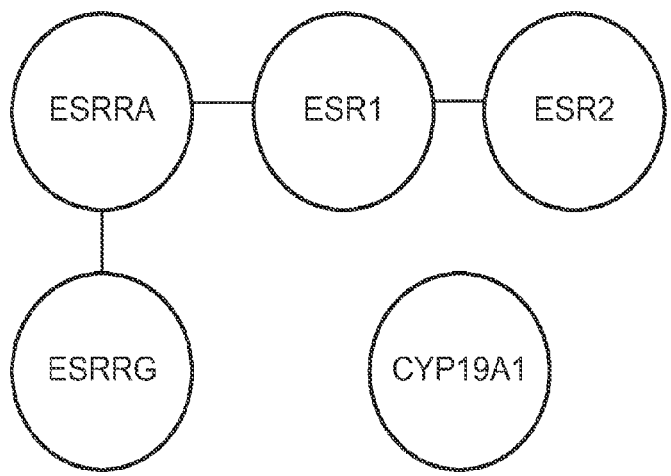
FIG. 1 depicts the development of an ER-centered network from 5 seed proteins using bioinformatic resources. (A) The five seed proteins used to build the ER-centered network. (B) The high confidence core results from making the ER-centered network. (C) The ER-centered network created from high confidence cores of each bioinformatic resource and the intersections among them.

An ER-centered network was developed using the open source software tool, Cytoscape. Creation of the ER-centered network began from 5 seed proteins: ESR1, ESR2, ESRRA, ESRRG and CYP19A1 (FIG. 1A). Bioinformatic databases were mined for protein-protein interactions (PPIs), protein complexes, members of canonical pathways linked with the 5 seed proteins and estrogen-responsive genes to complete the ER-centered network. These sources included BIND, BioGRID, DIP, HPRD, IntAct, MiMI, MINT, STRING, Biocarta, Linnea, Protein Lounge, STKE, Estrogen Responsive Genes Database (ERGDB) and literature searches (Table 1).

TABLE 1

ER-Centered Network Resources

Complexes

IntAct
PubMED literature search
Estrogen Responsive Genes

Estogen Responsive Genes Database
Pathways

Biocarta
Linnea
Protein Lounge
STKE
Protein-Protein Interactions

BIND
BioGRID
DIP
HPRD
IntAct
MiMI
MINT
STRING

The data from each bioinformatic resource was divided into 2 categories (1) a high confidence core group of proteins and (2) a secondary group associated with a lower confidence level. The core group from each data type was added to the network and proteins from the low-confidence group were added only if they were found to overlap with 1 of the other three data sources. PPI databases were mined for first and second neighbors of the five "seeds." The first neighbors (248) represent all proteins that are known to directly interact with at least one of the five seeds. They are the core of the PPI data and are part of the ER network. Second neighbors (5,592) are proteins that directly bind to first neighbors of the five seeds and comprise the lower-confidence group. All proteins found purified in a complex with one of the five seeds were added to the network. Protein designated by at least two different pathway sources as part of the ER signaling pathway belong to the high-confidence Pathway Core (44 genes) and all others represent the lower-confidence ER signaling pathway members. The Estrogen Responsive Gene Database (ERGD) Core represents the high-confidence genes that at least 2 papers found the gene to respond to an estrogen stimulus. Proteins that fell in the intersections among the lower-confidence data from the PPIs, Pathway analysis and ERGD were included in the network to complete the 631 gene ER-centered network.

Figure 1B:
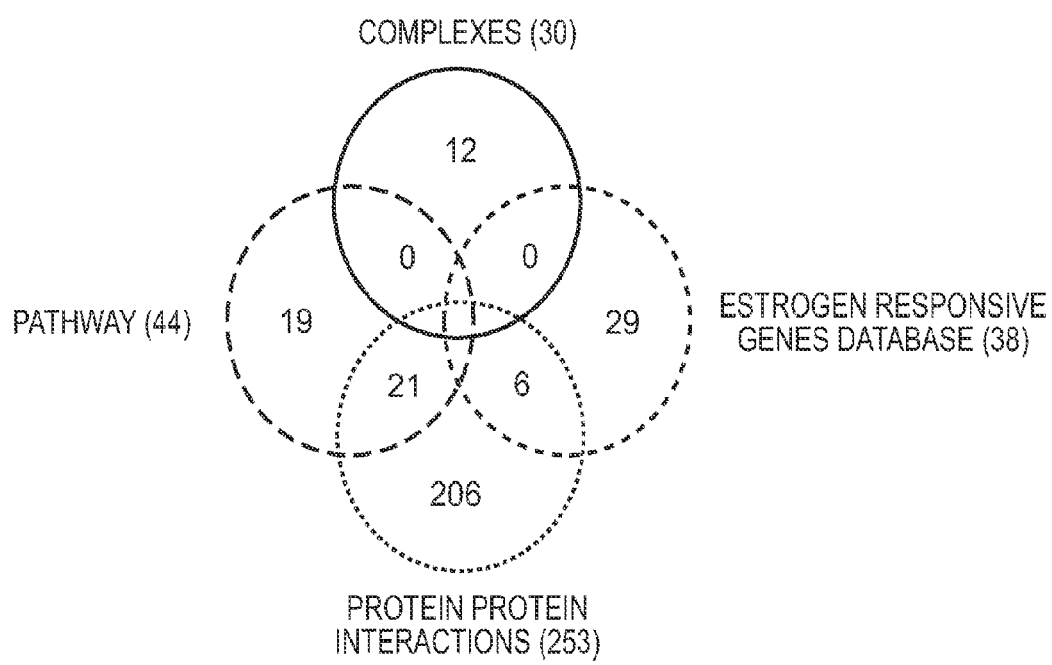

Combining the cores from each bioinformatic resource and the intersections among them, the ER-centered network has 631 non-redundant protein members. Proteins from the cores make up approximately half (49%) of the ER-centered network (FIG. 1B). Analysis of the proteins in the ER-centered network reveals the majority (97%) of the proteins in the ER-centered network are a first or second neighbor of the 5 seed proteins. Of those proteins, 32% and 34% are also associated with the ERGD and pathway dataset, respectively. Minimal overlap was found among three or more of the informatics resources used to create the ER-centered network (FIG. 1C) which highlights the utility in mining all of the bioinformatic resources used to create the ER-centered network.

An siRNA library was custom-ordered from Qiagen in a 96-well plate format with a single well representing one of the 631 genes identified as part of the ER-centered network. Each well contained 2 pooled siRNAs, each with different target sequences for the same gene, and was resuspended in RNase free water at 1 µM. Validated siRNA target sequences were preferentially picked when available. ER-centered library siRNAs were placed in 58 out of the inner 60 wells in eleven 96-well plates. The remaining 38 wells were left empty for controls.

Optimization was essential in preparing for the medium-throughput screening experiment. Reducing variability during the assay development stage improves the quality of the data set collected from screening. Specific to the aims of this study three things needed to be optimized before conducting a siRNA screen: selection of (1) a lipid transfection reagent, (2) moderate controls and (3) establishment of an assay Z'-factor.

Several reverse transfection reagents were tested in Costar 96-well plates with each cell line according to manufacturer's instructions. Transfection reagents tested included: DharmaFECT (DF) 1 from Dharmacon, DF 2, DF 3, DF 4, HiPerFect from Qiagen, RNAiFect from Qiagen, RNAiMAX from Invitrogen and siPORT from Applied Biosystems. Cells were seeded at a density that resulted in 80% confluency 144 hours post transfection (see Table 2). All-Star Negative (NEG), All-Star Death (DEATH) siRNAs from Qiagen were transfected at 20 nM and changes in cell viability with each transfection reagent was assessed after 144 hours post transfection. Cells were reverse transfected on day 0 with a total of 100.5 µL of volume in each well. After 24 hours, 100 µL of media was added for a total volume of 200.5 µL. On the seventh day, 20 µL of 1:1 mixture of Cell Titer Blue (CTB) from Promega and Hank's Buffered Salt Solution (HBSS) was added to each well and incubated for an optimized time interval between three and five hours before reading out the results using the EnVision Multilabel Plate Reader from PerkinElmer. This viability assay measures the metabolic activity of the living cells to covert resazurin to the fluorescent metabolite resorufin as an estimate of the number of viable cells. Fluorescence is recorded at room temperature using an excitation filter at 570 nm and an emission filter at 590 nm. An optimal transfection reagent for each cell line was selected based on three criteria: (1) transfection reagent alone had minimal affect on cell viability, (2) transfection reagent plus NEG had minimal affect on cell viability and (3) transfection reagent plus DEATH greatly reduced viability compared to NEG, DEATH/NEG≤0.2.

TABLE 2

| Cell Line | Media | Cell Seeding Density (96-well plate) cells/well | Transfection Reagent | Estrogen | Tamoxifen | Fulvestrant |
|---|---|---|---|---|---|---|
| MCF7 | IMEM 5% CCS 1 nM Estradiol | 7,000 | RNAiMAX | Dependent | Sensitive | Sensitive |
| LCC1 | IMEM 5% CCS | 2,000 | siPORT | Independent | Sensitive | Sensitive |
| LCC9 | IMEM 5% CCS | 2,000 | siPORT | Independent | Cross-resistant | Resistant |
| T47D | IMEM 5% CCS 1 nM Estradiol | 3,000 | HiPerfect | Dependent | Sensitive | Sensitive |
| T47Dco | IMEM 5% CCS | 3,000 | RNAiMAX | Independent | Resistant | Resistant |
| BT474 | IMEM 5% CCS 1 nM Estradiol | 10,000 | Lipofectamine 2000 | Dependent | Sensitive | Sensitive |
| MCF10A | DMEM/F12 5% HS | 7,000 | Lipofectamine 2000 | | | |
| HFF1 | DMEM 15% FBS | 8,000 | Dharmafect 3 | NA | NA | NA |
| MDA MB 231 | | | | Independent | NA | NA |

Figure 2A:
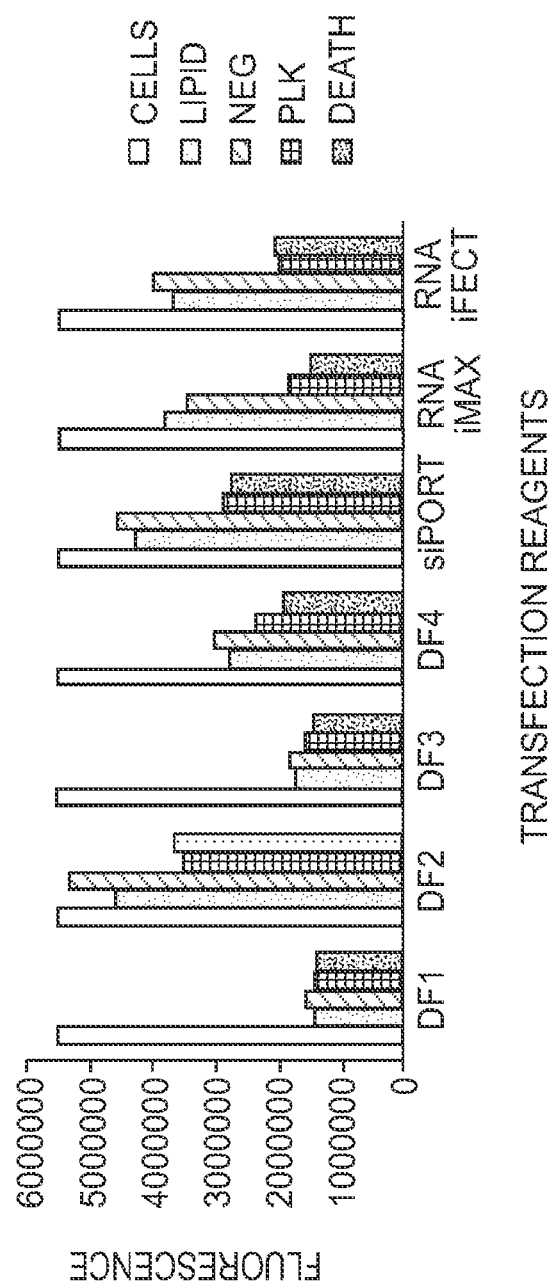
FIG. 2 depicts screening optimization. (A) Viability of MCF7 cells to determine the best transfection reagent for each cell line. RNAiMAX was selected for the MCF7 cells. (B) LCC1 cells were transfected with siRNAs to select for moderate controls during screening to assess inter-plate and inter-screen variability.
Figure 2B:
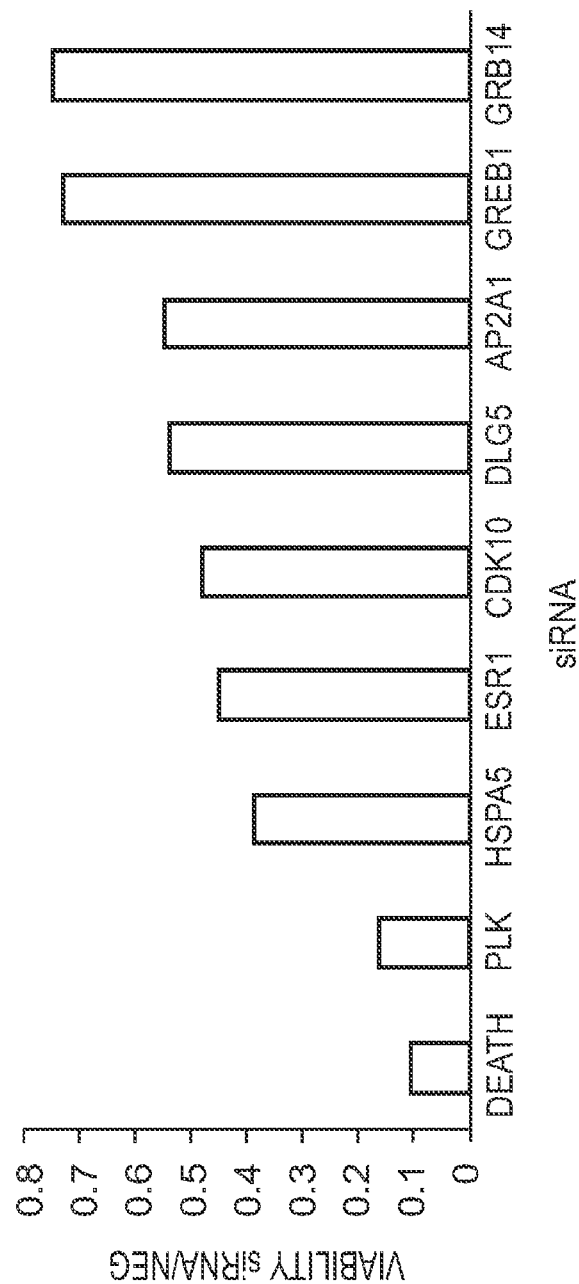

To identify an effective transfection reagent, eight different lipid based transfection reagents were tested for their ability to reverse transfect MCF7, LCC1, LCC9 and HFF1 cell lines. FIG. 2, shows results from this test for the MCF7 cell line. Assessment of the reagents was based on the fluorescence readout using the cell titer. Two controls from Qiagen were used: All-Star Negative control, a non-silencing siRNA with no known homology to a mammalian gene, and All-Star Death control, a combination of several siRNAs targeting genes essential for cell survival, to assess the transfection reagents. RNAiMAX was chosen as the best transfection reagent for the MCF7 cell line. Transfection reagents for each cell line were selected to have a minimal effect on cell viability with the lipid alone and in combination with the All-Star Negative control compared to untreated cells. Furthermore, at least an 80% reduction in cell viability was observed with All-Star Death control relative to the All-Star Negative control.

siRNAs moderately effecting cell viability were established for inter-plate variability assessment during screening. Ten siRNAs that moderately reduced cell viability in 4 different cell lines were knocked-down in LCC1 cells and the effects on cell viability were measured. siRNAs for genes GRB14 and AP2A1 were selected for their ability to modestly reduce cell viability in LCC1 cells (FIG. 2B) and then tested to confirm these siRNAs as moderate controls for MCF7, LCC9 and HFF1 cells.

MCF7 and HFF1 cell lines used in these studies were obtained from the Tissue Culture Shared Resource at Lombardi Comprehensive Cancer Center, Georgetown University and the LCC1 and LCC9 cell lines were a gift from Robert Clarke (Lombardi Comprehensive Cancer Center, Georgetown University). Cell lines were maintained at 37° C. and 5% CO2. HFF1 cells were cultured in DMEM with 15% FBS. MCF7 cells were cultured in phenol-red free IMEM from Invitrogen with 5% charcoal-stripped calf serum (CCS) and 1 nM estradiol. The LCC1 and LCC9 cell lines are MCF7 variants that maintain ER expression, however, both cell lines are estrogen independent. These cell lines were cultured in phenol-red free IMEM with 5% CCS. The LCC1 cell line is sensitive to Fulvestrant while the LCC9 cell line is resistant to the ER antagonist.

ER-centered library screens were carried out using MCF7, LCC1, LCC9 and HFF1 cell lines. Cells were seeded in 96 well plates at a density that resulted in a final well confluency of approximately 80%. Cells were reversed transfected with the ER-centered siRNA library at 20 nM in duplicate and incubated at 37° C. and 5% CO2 for 144 hours. After 24 hours, 100 μL of the appropriate media were added to each well of the arrayed screen. On the seventh day, 20 μL of 1:1 mixture of Cell Titer Blue (CTB) from Promega and Hank's Buffered Salt Solution (HBSS) was added to each well and incubated for another 4 hours before reading out the results using the EnVision Multilabel Plate Reader from PerkinElmer. This viability assay measures the metabolic activity of the living cells to covert resazurin to the fluorescent metabolite resorufin as an estimate of the number of viable cells. Fluorescence is recorded at room temperature using an excitation filter at 570 nm and an emission filter at 590 nm.

Viability for each targeted gene was calculated by normalizing to median fluorescence value of 14 non-silencing controls on the plate. Hits for further investigation were selected if siRNA knock-down reduced viability by greater than 50%.

Figure 3A:
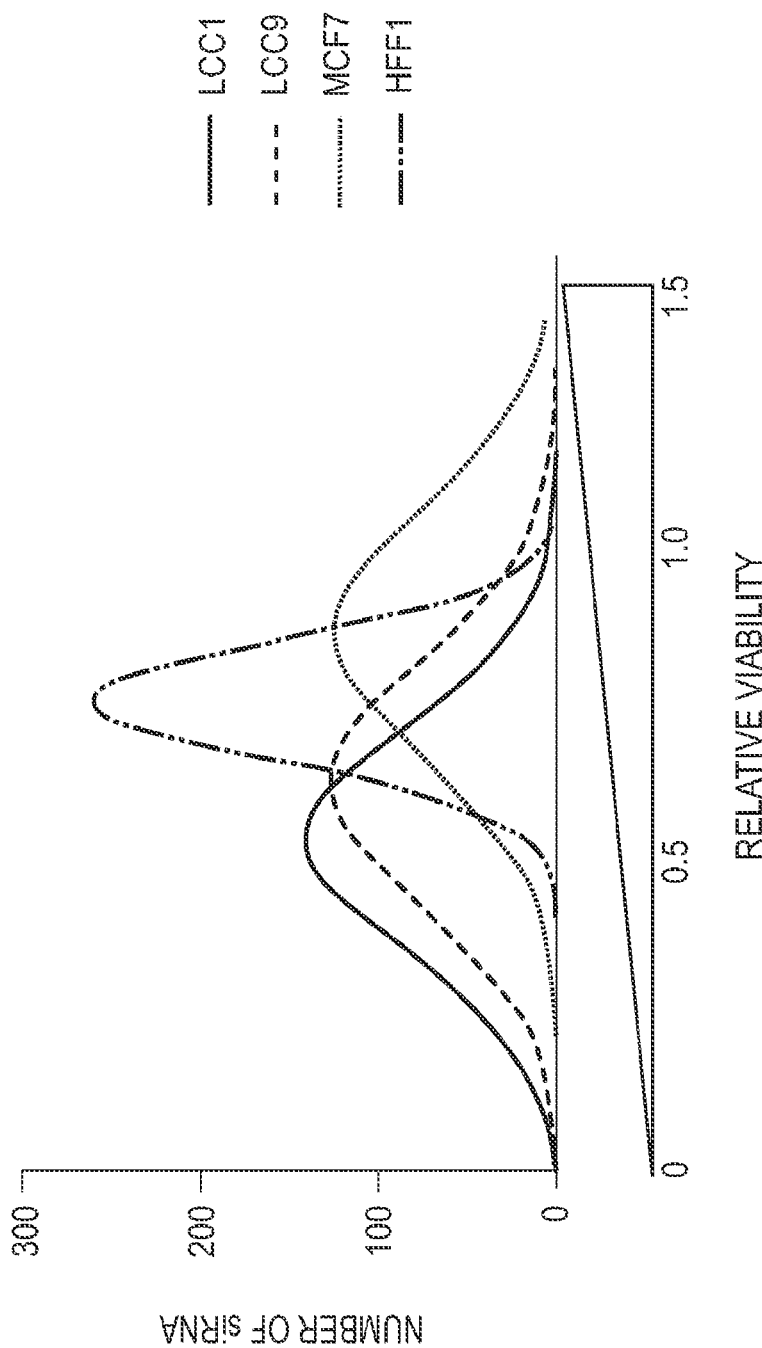
FIG. 3 depicts ER-centered siRNA screens with breast cancer and normal cell lines. (A) Distribution plots of relative viability from ER-centered siRNA screens with breast cancer and normal cells. (B) Hits representing a reduction in viability by greater than 50% for each of the cell lines screened with the ER-centered library. The 190 putative hits identified for LCC1 cell were selected for validation. (C) Validated hit results in LCC1 cells.
Figure 3B:
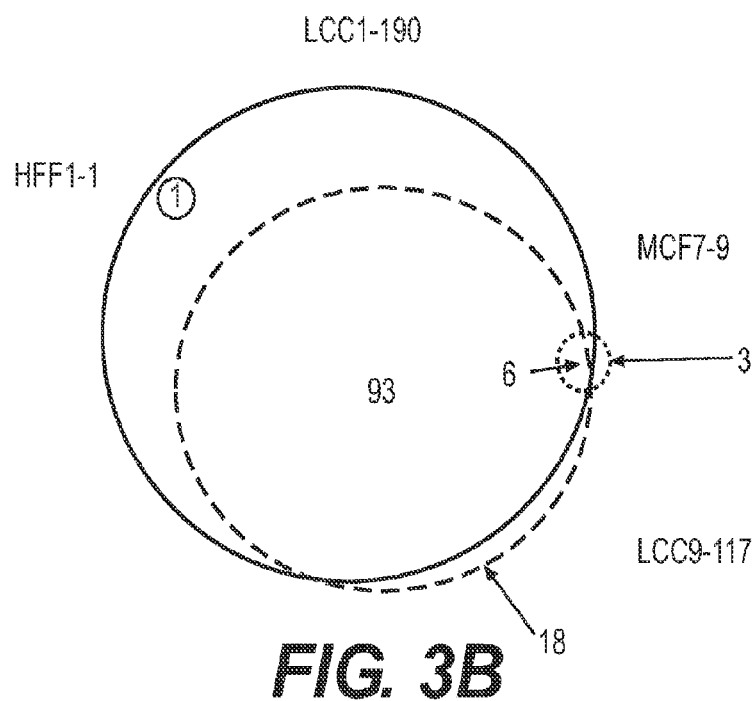

For each of the ER-centered network screens carried out using MCF7, LCC1, LCC9 and HFF1 cells a distribution plot was created to from the normalized viability calculated (FIG. 3A). The knock-down of individual genes in the ER-centered network cause the viability distribution for LCC1 and LCC9 cell lines to shift to the left compared to the parental cell line MCF7. These estrogen independent cell lines are more susceptible to the knock-down of genes in the ER-centered network. In comparison, the HFF1, the normal-like control cell line, is moderately affected by the knock-down of ER-centered network genes. A biological cut-off at less than 50% viability, identifies 190 putative hits for the LCC1 cells, 117 for LCC9 cells, 9 for MCF7 cells and 1 for HFF1 cells (FIG. 3B).

Hits identified as a loss of 50% viability by siRNA knock-down in LCC1 cells were further studied for validation. For each hit identified four different siRNAs targeting the same gene were tested in individual wells. The siRNAs were order from Qiagen. Two out of the four siRNAs were the same target sequences as the siRNAs in the screen, when available. The other two siRNAs were new sequences to test and priority was placed on validated sequences by Qiagen when available.

LCC1 cells were seeded in 96 well plates at a density that resulted in a final well confluency of approximately 80%. Cells were reversed transfected with siRNAs at 20 nM in duplicate and incubated at 37° C. and 5% CO2 for 144 hours. After 24 hours, 100 µL of phenol red-free IMEM+5% charcoal stripped calf serum was added to each well of the arrayed validation screen. On the seventh day, 20 µL of 1:1 mixture of Cell Titer Blue (CTB) from Promega and Hank's Buffered Salt Solution (HBSS) was added to each well and incubated for another 4 hours before reading out the results using the EnVision Multilabel Plate Reader from PerkinElmer. Viability for each siRNA gene was calculated by normalizing to median fluorescence value of 14 non-silencing controls on the plate. A putative hit passed validation, if at least two out of four of the siRNAs tested reduced viability by 50% or more.

Figure 3C:
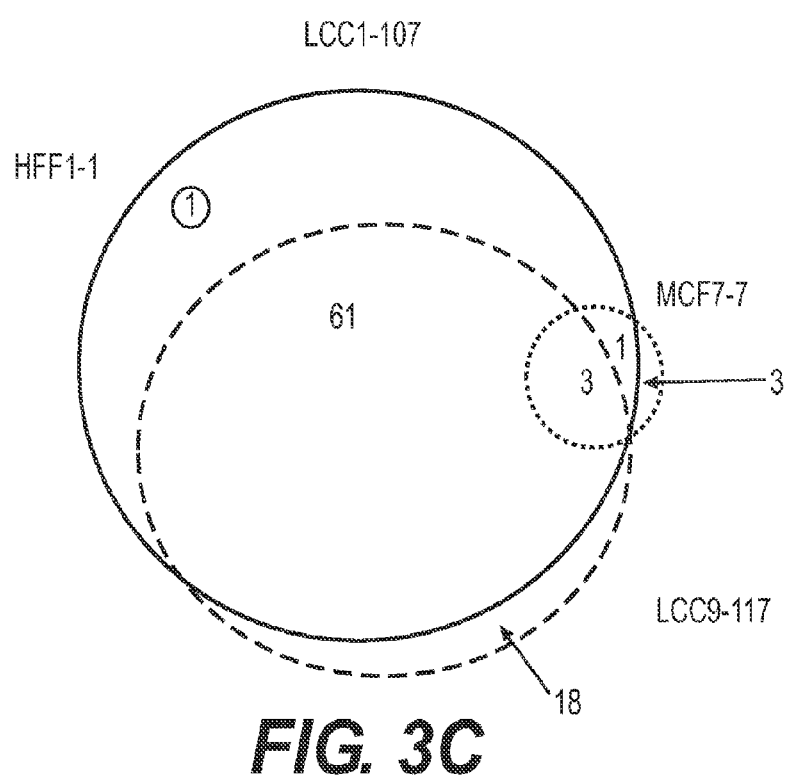

Hits identified as reducing viability by more than 50% in LCC1 cells were furthered studied for validation. Of the 190 hits defined in LCC1 cells, 107 of the hits passed validation with at least two out of four siRNAs reducing viability by 50% (FIG. 3C).

Essential Genes for Estrogen Independent Cell Lines

In addition to measuring the changes in viability for LCC1, LCC9, MCF7 and HFF1 cells, five breast cell lines were studied to understand how individual knock-downs of 27 genes identified to be essential in estrogen independent LCC1 and LCC9 cell lines may affect a variety of breast cancer subtypes. (Table 3). Cells were seeded in 96 well plates at a density that resulted in a final well confluence of approximately 80%. Cells were reversed transfected with siRNAs at 20 nM in triplicate and incubated at 37° C. and 5% CO2 for 144 hours. After 24 hours, 100 µL of the appropriate medium was added to each well of the arrayed validation screen. On the seventh day, 20 µL of 1:1 mixture of Cell Titer Blue (CTB) from Promega and Hank's Buffered Salt Solution (HBSS) was added to each well and incubated for another 4 hours before reading out the results using the EnVision Multilabel Plate Reader from PerkinElmer. Viability for each gene knock-down was calculated by normalizing to median fluorescence value of 16 non-silencing controls on the plate.

TABLE 3

| Gene Symbol | Gene Name |
|---|---|
| BLOC1S1 | biogenesis of lysosome-related organelles complex-1, subunit 1 |
| CDC2L1 | cell division cycle 2-like 1 (PITSLRE proteins) |
| CNOT1 | CCR4-NOT transcription complex, subunit 1 |
| CYR61 | cysteine-rich, angiogenic inducer, 61 |
| DDX54 | DEAD (Asp-Glu-Ala-Asp) box polypeptide 54 |
| EIF3I | eukaryotic translation initiation factor 3, subunit 2 beta, 36 kDa |
| FANCG | Fanconi anemia, complementation group G |
| FBP1 | fructose-1,6-bisphosphatase 1 |
| IER2 | immediate early response 2 |
| KIF1A | kinesin family member 1A |
| LCK | lymphocyte-specific protein tyrosine kinase |
| NR2F1 | nuclear receptor subfamily 2, group F, member 1 |
| PNRC1 | proline-rich nuclear receptor coactivator 1 |
| POLR2A | polymerase (RNA) II (DNA directed) polypeptide A, 220 kDa |
| POLR2B | polymerase (RNA) II (DNA directed) polypeptide B, 140 kDa |
| POLR2C | polymerase (RNA) II (DNA directed) polypeptide C, 33 kDa |

TABLE 3-continued

| Gene Symbol | Gene Name |
|---|---|
| PRPF6 | PRP6 pre-mRNA processing factor 6 homolog (*S. cerevisiae*) |
| PSMB4 | proteasome (prosome, macropain) subunit, beta type, 4 |
| PSMC5 | proteasome (prosome, macropain) 26S subunit, ATPase, 5 |
| PSMD1 | proteasome (prosome, macropain) 26S subunit, non-ATPase, 1 |
| PTK7 | PTK7 protein tyrosine kinase 7 |
| RPS2 | ribosomal protein S2 |
| SCNN1A | sodium channel, nonvoltage-gated 1 alpha |
| SF3A3 | splicing factor 3a, subunit 3, 60 kDa |
| TAF2 | TAF2 RNA polymerase II, TATA box binding protein (TBP)-associated factor, 150 kDa |
| TOB1 | transducer of ERBB2, 1 |
| TSC22D4 | TSC22 domain family, member 4 |

Figure 4A:
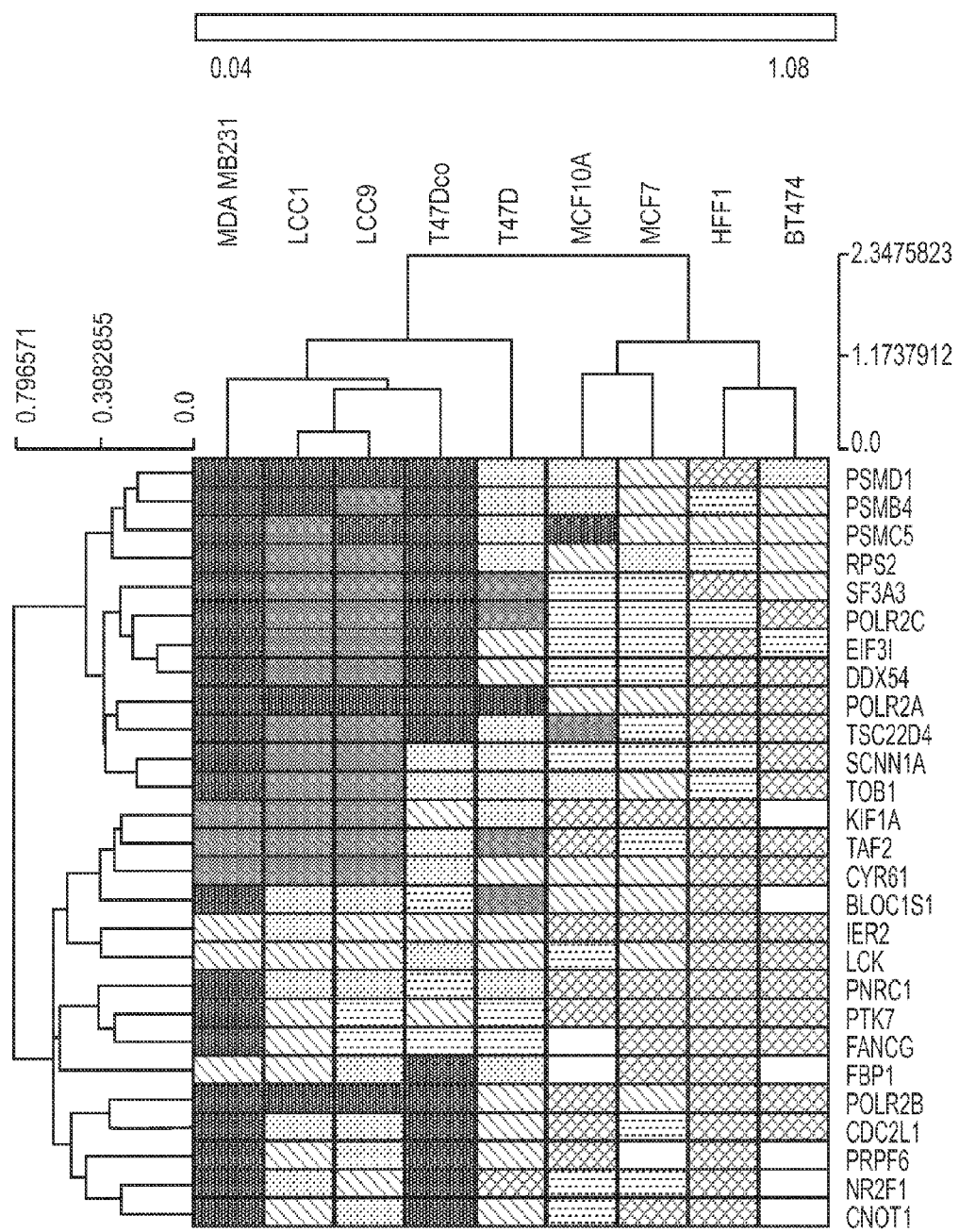
FIG. 4 depicts essential genes for survival of Estrogen-Independent Cell Lines (A) Heatmap representing the viability of breast cancer and normal like cell lines after gene knockdown. Clusters were identified using hierarchical clustering based on average linkage and Euclidean distance. (B) Exposure to estradiol does not change the effect of the knock of PSMD1, one of the genes in the essential gene subset in estrogen independent cell lines LCC1 and LCC9. (C) Over 50% of the individual knock-down of the genes in the essential gene subset induce caspase 7 activity by 2 fold or great in LCC1 and LCC9 cells. (D) Both apoptosis inducing, PSMD1, and non-apoptosis inducing, TOB1, have a reduction in proliferation 144 h post transfection.

A subset of validated hits was selected, which represented a range of viability for 0.1-0.49 that were identified as being essential for estrogen independent breast cancer cell lines LCC1 and LCC9. FIG. 4A is a heatmap that shows the effect of individual knock-down the subset of genes across breast cancer and normal-like cell lines. The estrogen receptor positive, estrogen independent cell lines cluster together toward the left of the heat map. The triple negative, estrogen independent cell line, MDA MB 231, also clusters with those cell lines on the left. The viability of these estrogen independent breast cancer cell lines are sensitive to knock-down of these genes. While the estrogen receptor positive and normal-like all cluster on the right of the heatmap and are associated with higher viability.

LCC1 and LCC9 cells were cultured in IMEM+5% CCS and IMEM+5% CCS or 1 nM estradiol. MCF7 cells were cultured in IMEM+5% CCS and 1 nM estradiol. Cells were seeded in 96 well plates at a density that resulted in a final well confluency of approximately 80%. Cells were reversed transfected with siRNAs at 20 nM in triplicate and incubated at 37° C. and 5% CO2 for 144 hours. After 24 hours, 100 µL of the appropriate medium was added to each well of the 96-well assay plate. On the seventh day, 20 µL of 1:1 mixture of Cell Titer Blue (CTB) from Promega and Hank's Buffered Salt Solution (HBSS) was added to each well and incubated for another 4 hours before reading out the results using the EnVision Multilabel Plate Reader from PerkinElmer. Viability for each gene knock-down was calculated by normalizing to median fluorescence value of 16 non-silencing controls on the plate.

Figure 4B:
Figure 5:
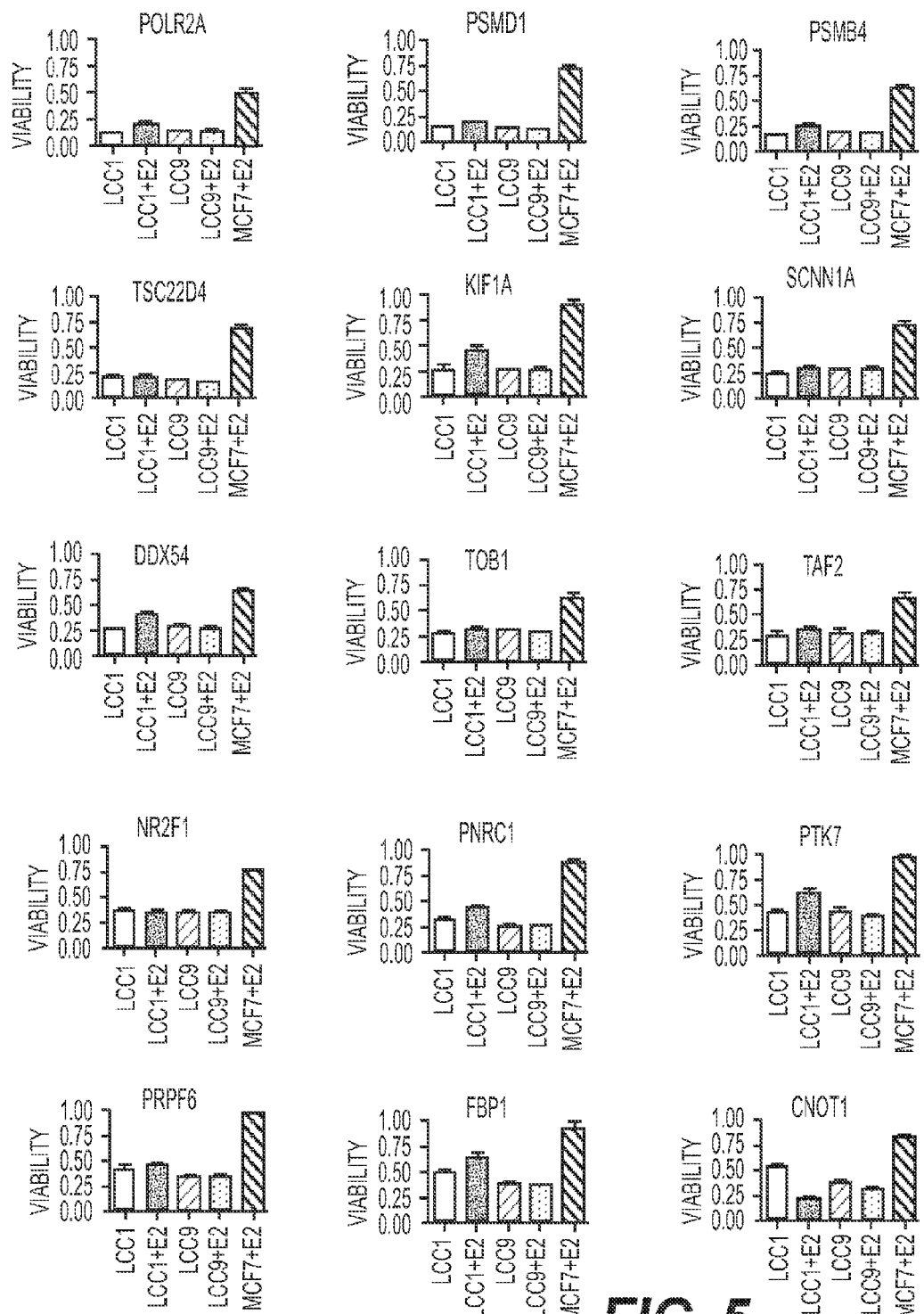
FIG. 5 depicts estradiol exposure to estrogen independent LCC1 and LCC9 cell line not changing the effect on viability with individual gene knock-down of the essential gene subset.
Figure 5:
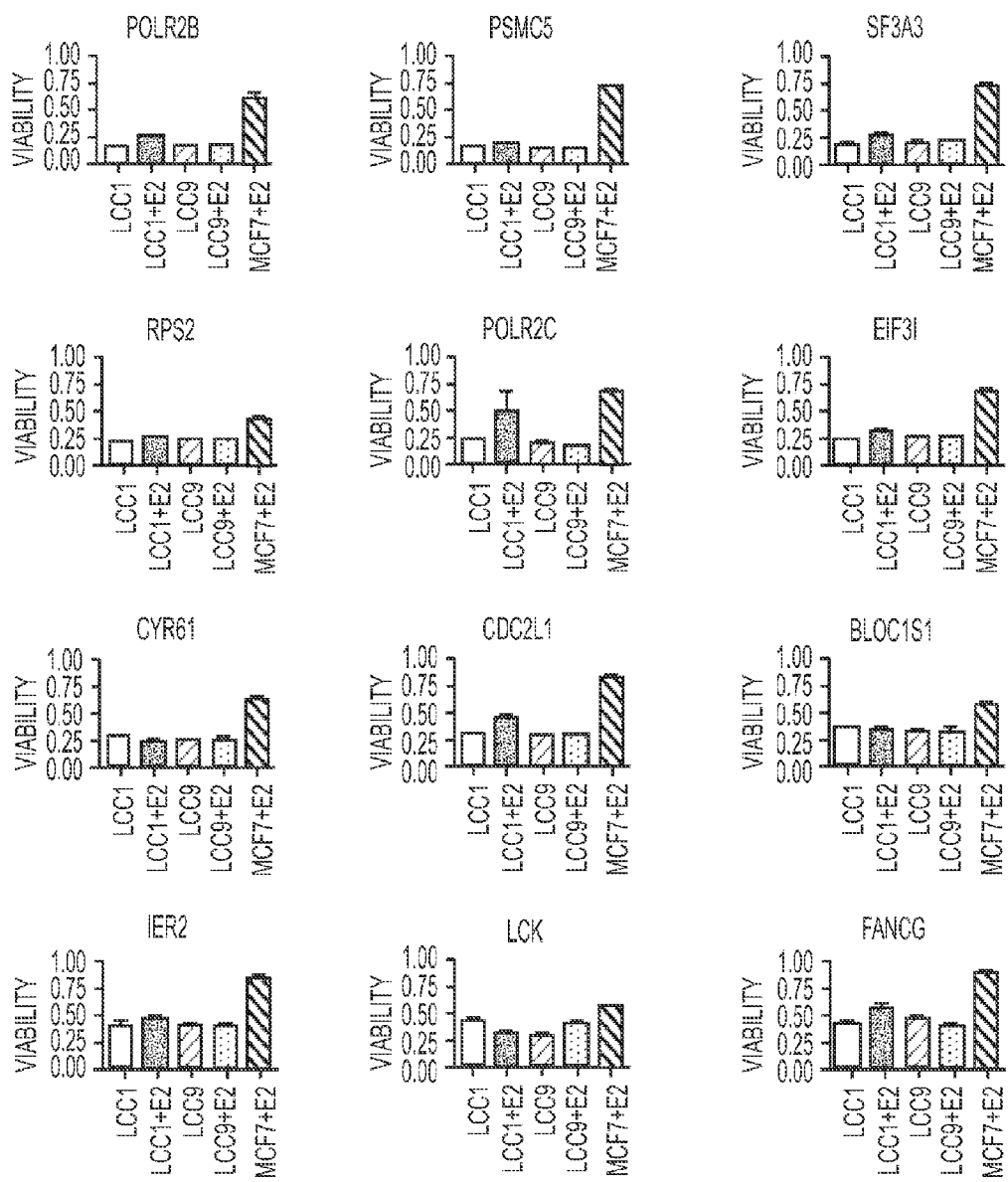

Estrogen independent breast cancer cell line LCC1 and LCC9 cultured in 1 nM estradiol resulted in no significant change in viability after individual knock-down of the genes in the essential gene subset. These result show a clear difference in viability between the estrogen independent cell lines and the parental, estrogen dependent MCF7 cell line in response to individual gene knock-down, as seen in FIG. 4B, the knockdown of PSMD1. All results of these studies can be seen in FIG. 5.

LCC1 and LCC9 cells were seeded at 6,250 cells per well. Cells were reversed transfected with siRNAs at 20 nM in triplicate and incubated at 37° C. and 5% CO2 for 120 hours. On the sixth day, caspase 7 activity was measured using Apo-ONE as described by Promega. Fluorescence was measured using the EnVision Multilabel Plate Reader from PerkinElmer. Caspase 7 activity for each gene knock-down was calculated by normalizing to median fluorescence values of non-silencing controls on the plate.

Estrogen independent cell lines, LCC1 and LCC9, were further studied to understand the mechanisms by which a reduction in viability was observed. Caspase 7 activity was measured as an indicator of apoptotic activity. Over 50% of the essential genes identified induce caspase 7 activity by at least two-fold when knocked-down. The knock-down of CNOT1, known to function as a transcriptional regulator, induces a 20 fold increase in caspase 7 activity.

The individual knock-down of the genes in the essential gene subset all reduce proliferation in estrogen independent breast cancer cells LCC1 cells were seeded at 2,000 cells per well. Cells were reversed transfected with siRNAs at 20 nM in triplicate and incubated at 37° C. and 5% CO2 for 24 h, 48 h, 72 h, 96 h, 120 h or 144 h. Every 24 h post transfection, proliferation was measured using BrdU incorporation as described by Roche. Luminescence was measured using the EnVision Multilabel Plate Reader from PerkinElmer. BrdU incorporation for each gene knock-down was calculated by normalizing to median luminescence values of non-silencing controls on the plate.

Figure 4D:
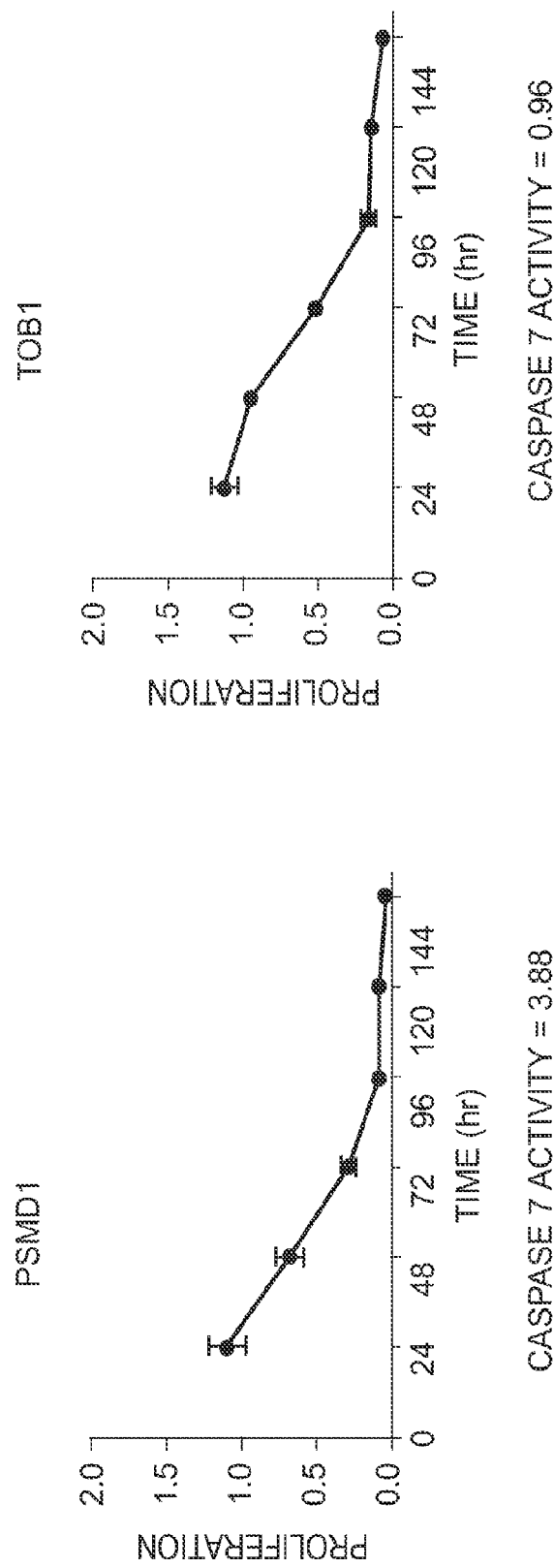
Figure 6:
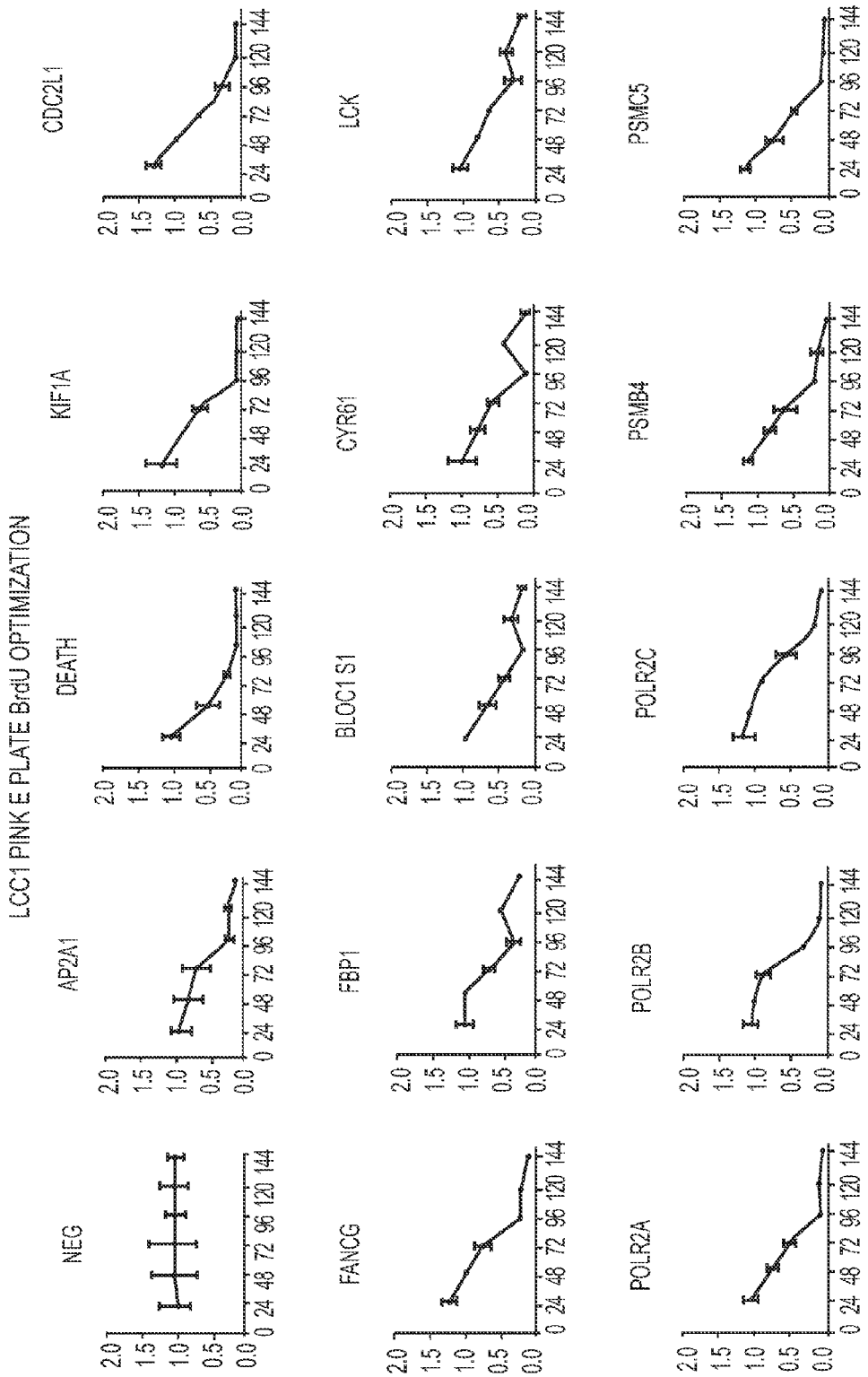
FIG. 6 depicts over 144 h, the individual knock-down of all of the essential gene subset reduces proliferation.
Figure 6:
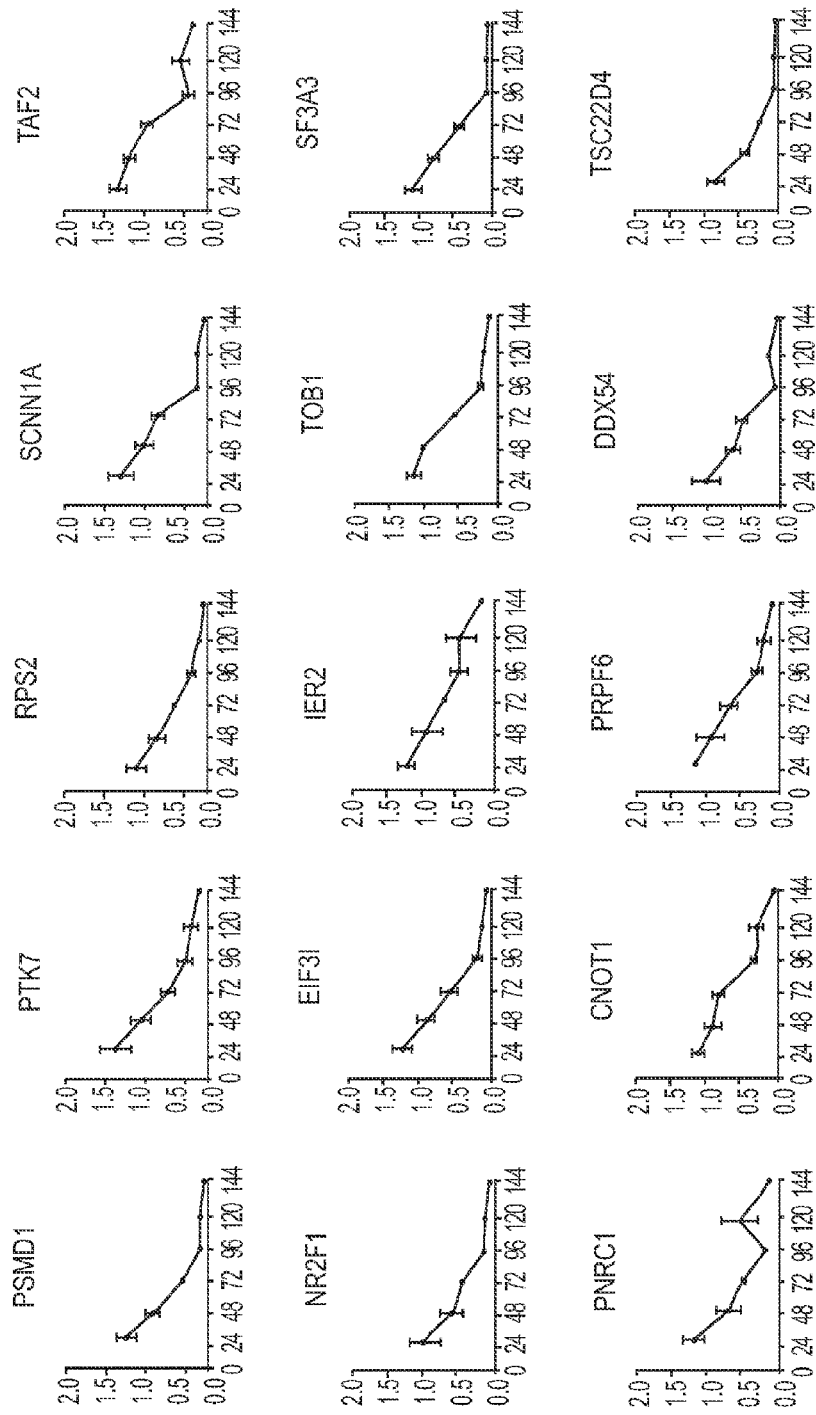

A reduction in proliferation was observed by 144 h post transfection for each gene in the essential gene subset. This observation was seen in both the apoptosis inducing and non-apoptosis inducing groups within the essential gene subset (FIG. 4D). All of the data can be seen in FIG. 6.

The list of genes in the essential genes subset was submitted into STRING to identify only experimentally verified protein-protein interactions. Nodes in the ER-centered network were analyzed for degree centrality to identify hubs.

Figure 7A:
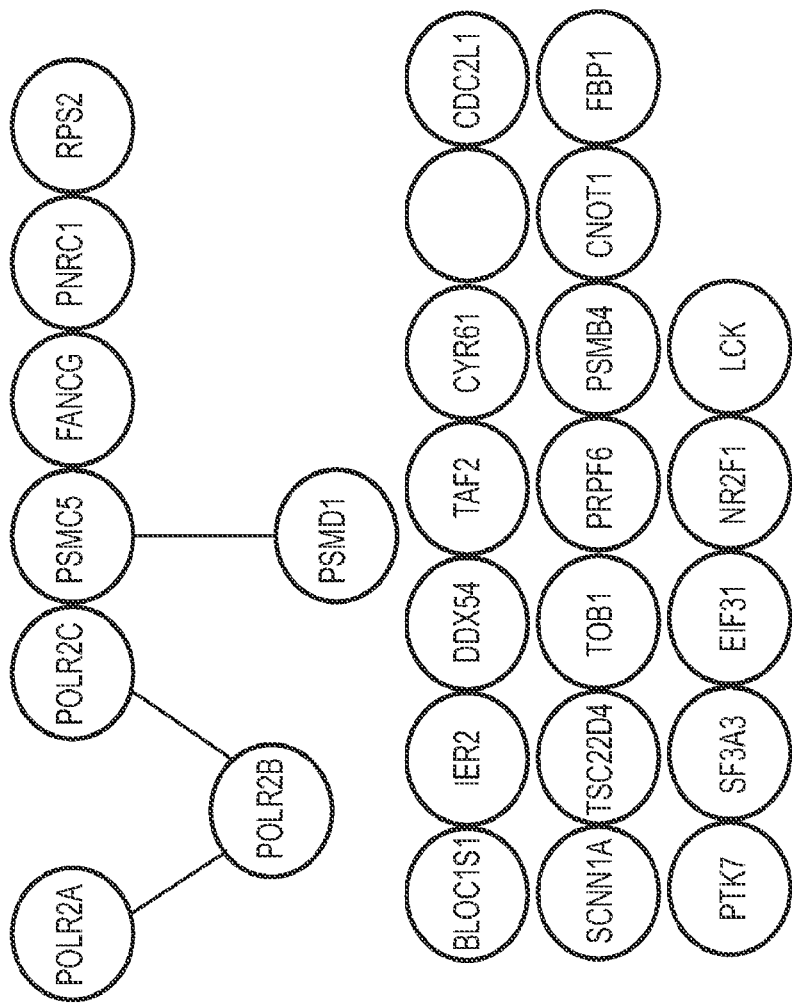
FIG. 7 depicts protein interactions. (A) Experimentally verified protein-protein interactions among the genes in the essential genes subset. (B) The essential gene subset (dark nodes) and the first neighbors (light nodes) within the ER-centered network based on experimentally verified protein-protein interactions. (C) Breakdown of the essential gene subset within the sub groups that were used to create the network.

Based on experimentally verified protein-protein interactions in the STRING database, the essential gene subset does not form a network. There are a few protein-protein interactions among the 27 genes in the essential gene subset; mostly family members interacting with one another (FIG. 7A). The genes in the essential gene subset are, however, connected to nodes with higher degree centrality within the ER-centered network (FIG. 7B). Hubs were identified in the ER-centered network as the top 5% of the nodes with highest degree. There were 32 hubs in the ER-centered network and none of the genes in the essential gene subset are a hub.

Mapping the essential genes subset back to the resources that were used to create the ER-centered network showed that all but one of genes are a first or second neighbor of 5 seed genes used to generate the network (FIG. 7C). None of the genes in the essential gene subset are from the complex data included in the network. There is slight increase in the representation of the overlap between the PPI and Estrogen Responsive Genes Data set in the essential genes subset (37%) compared to the ER-centered network (31%). A 15% increase in representation of the nodes that are only from the PPI data is observed in the essential genes subset (41%) compared to ER-centered network (26%).

LCC1, LCC9 and MCF7 cells were seeded at density so that the untreated condition was at 80% confluence on day 7 in the appropriate medium. Cells were incubated at 37° C. and 5% CO2 for 7 days. Twenty-four hours later, cells were treated with Bortezomib with final well concentrations ranging from 2.5 nM-2.5 µM. On the seventh day, 20 µL of 1:1 mixture of Cell Titer Blue (CTB) from Promega and Hank's Buffered Salt Solution (HBSS) was added to each well and incubated for another 4 hours before reading out the results using the EnVision Multilabel Plate Reader from PerkinElmer. Viability was calculated as a percentage of the untreated cells.

Figure 8:
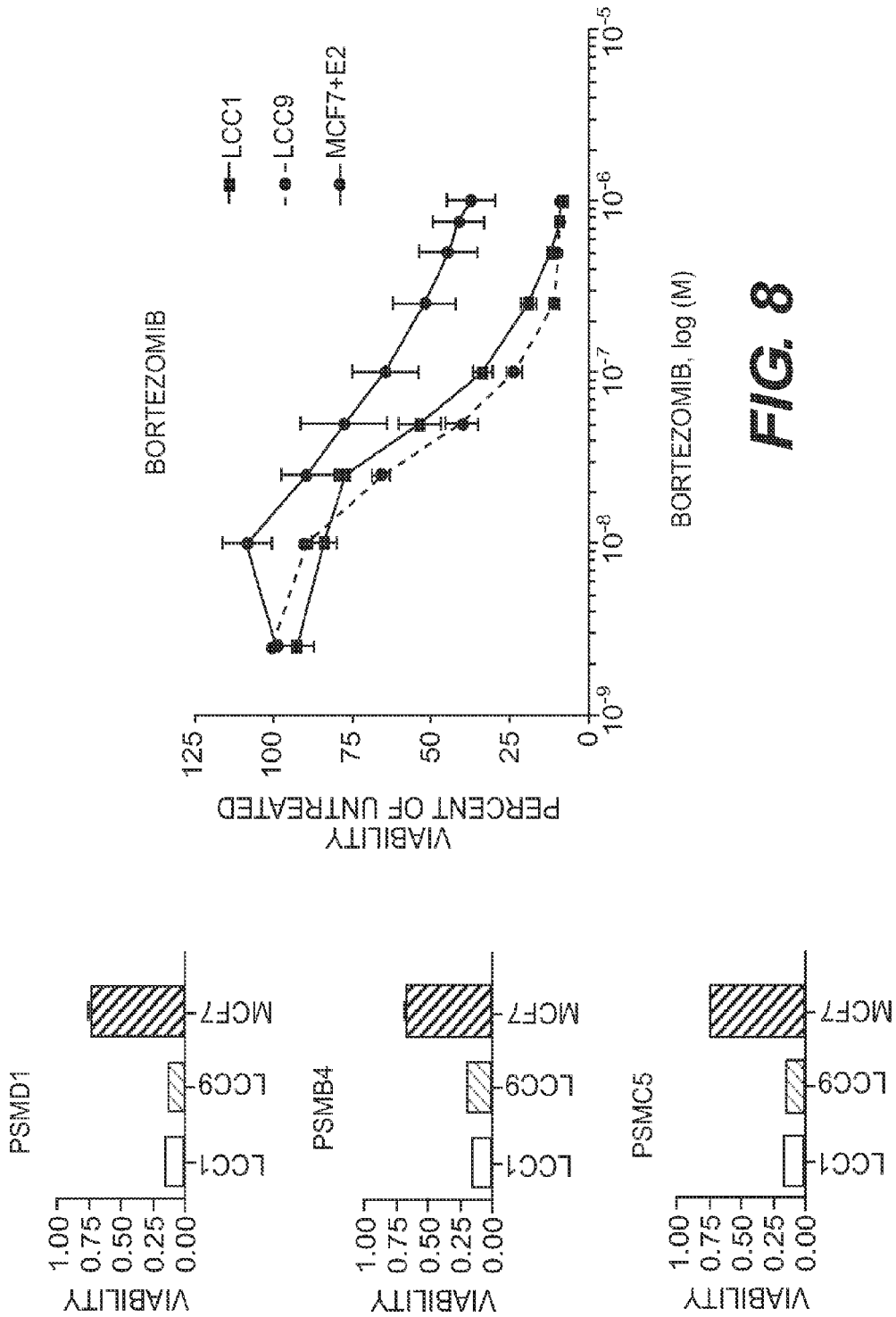
FIG. 8 depicts proteasome inhibitor is more effective in reducing viability in estrogen independent breast cancer cell lines.
Figure 9:
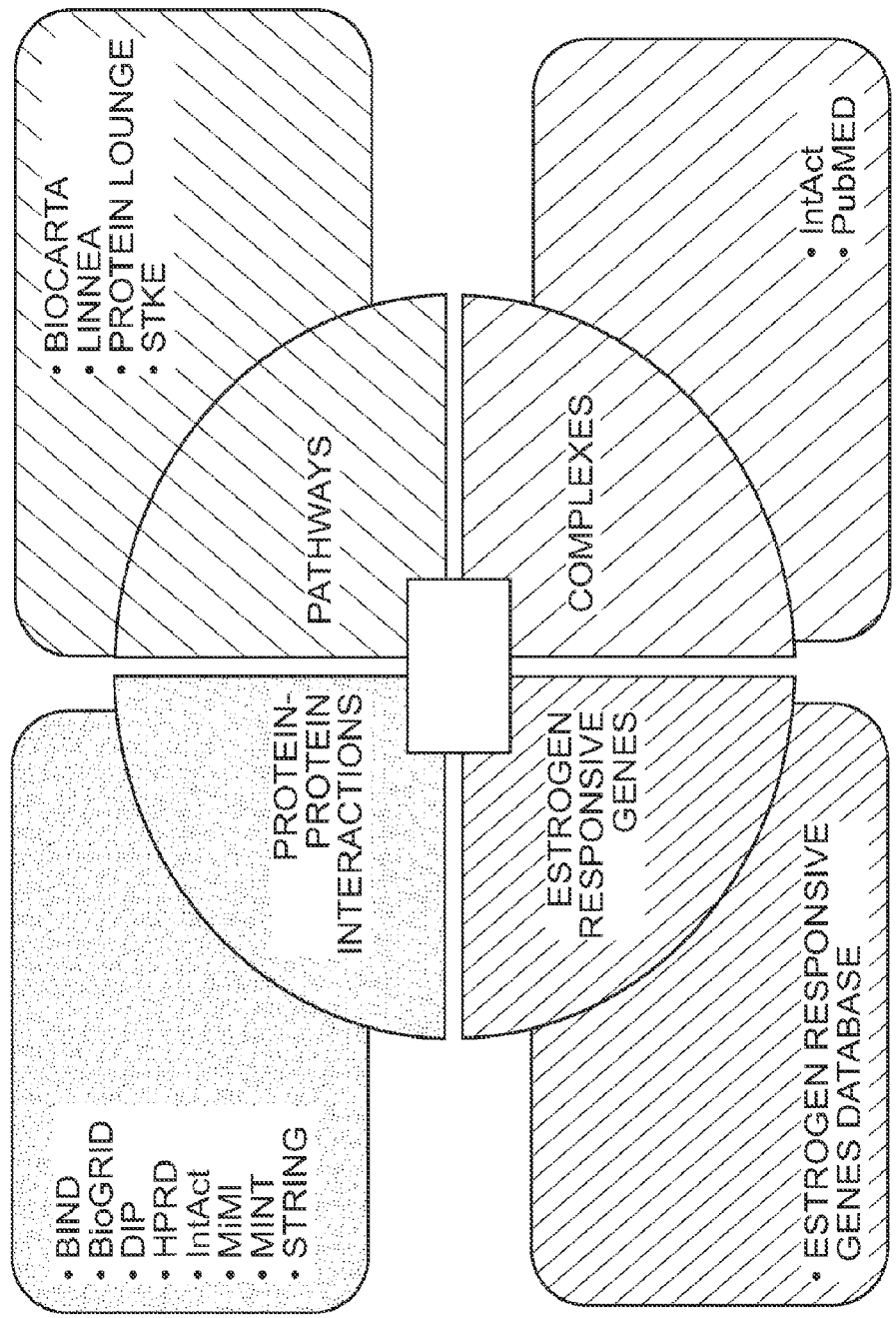
FIG. 9 depicts ER-Centered Network Sources.
Figure 10:
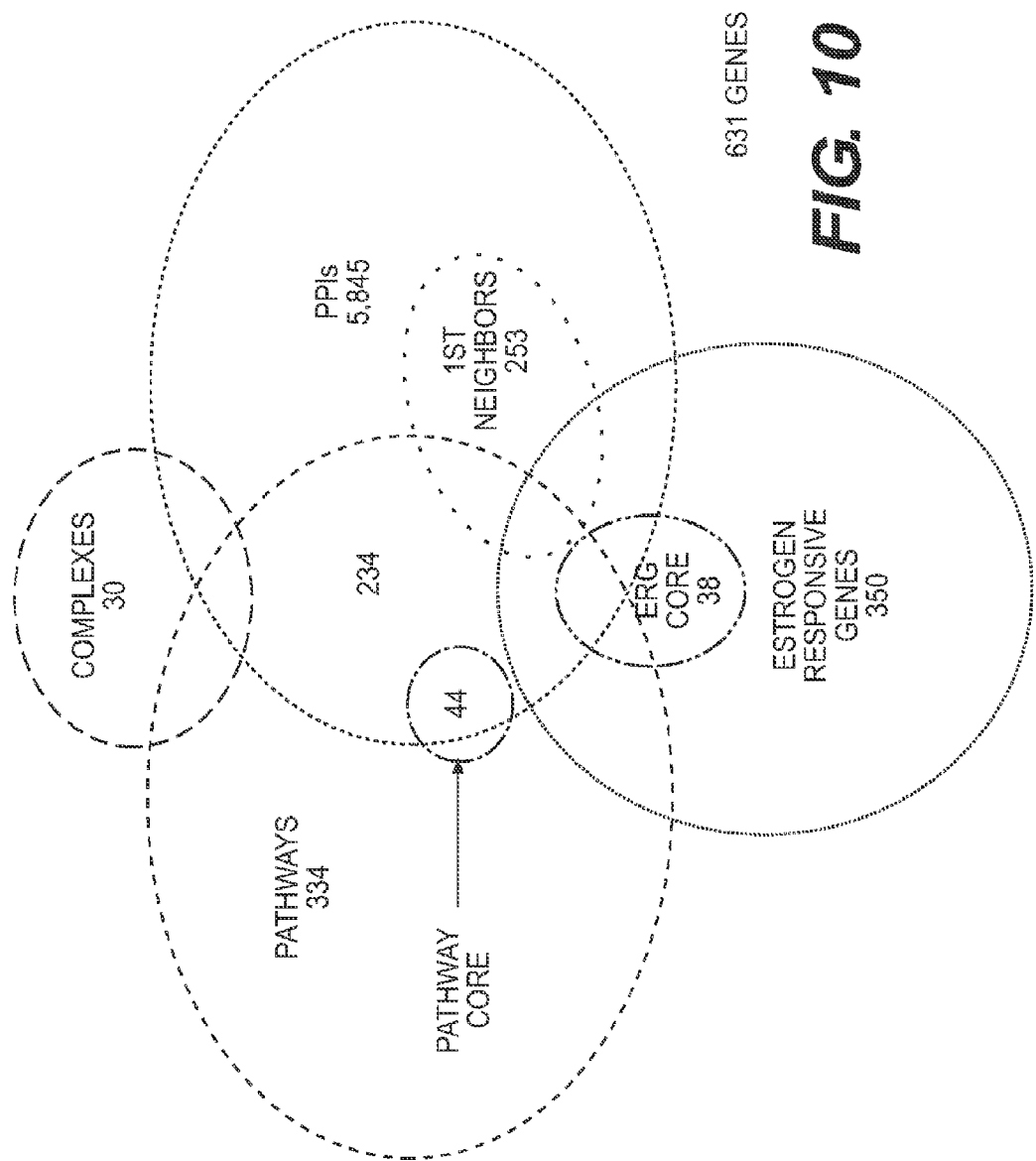
FIG. 10 depicts protein-protein interactions (PPIs), Pathways, Complexes and Estrogen Responsive Gene
Figure 11:
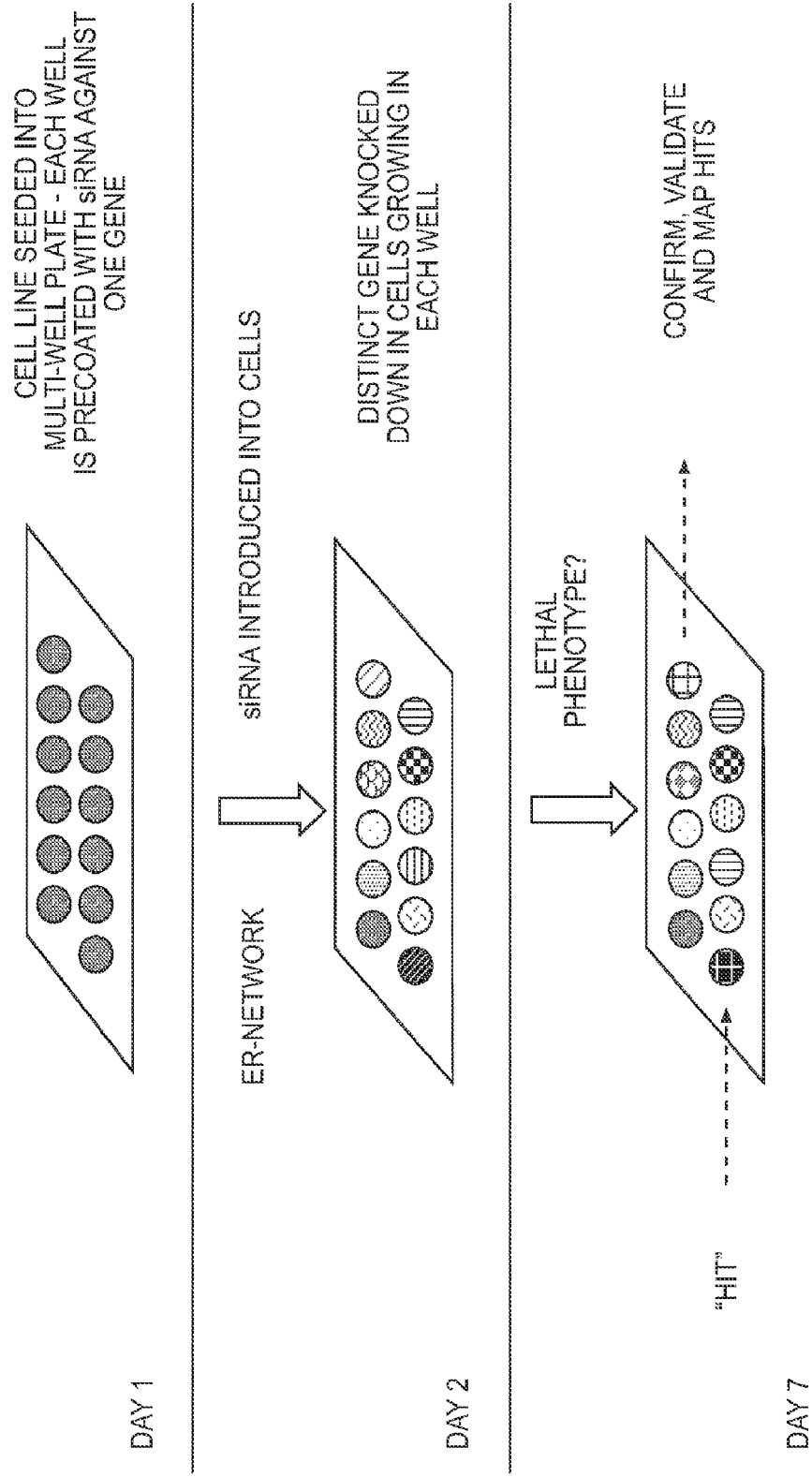
FIG. 11 depicts a flow diagram of the siRNA screening assay used in the present invention.
Figure 12:
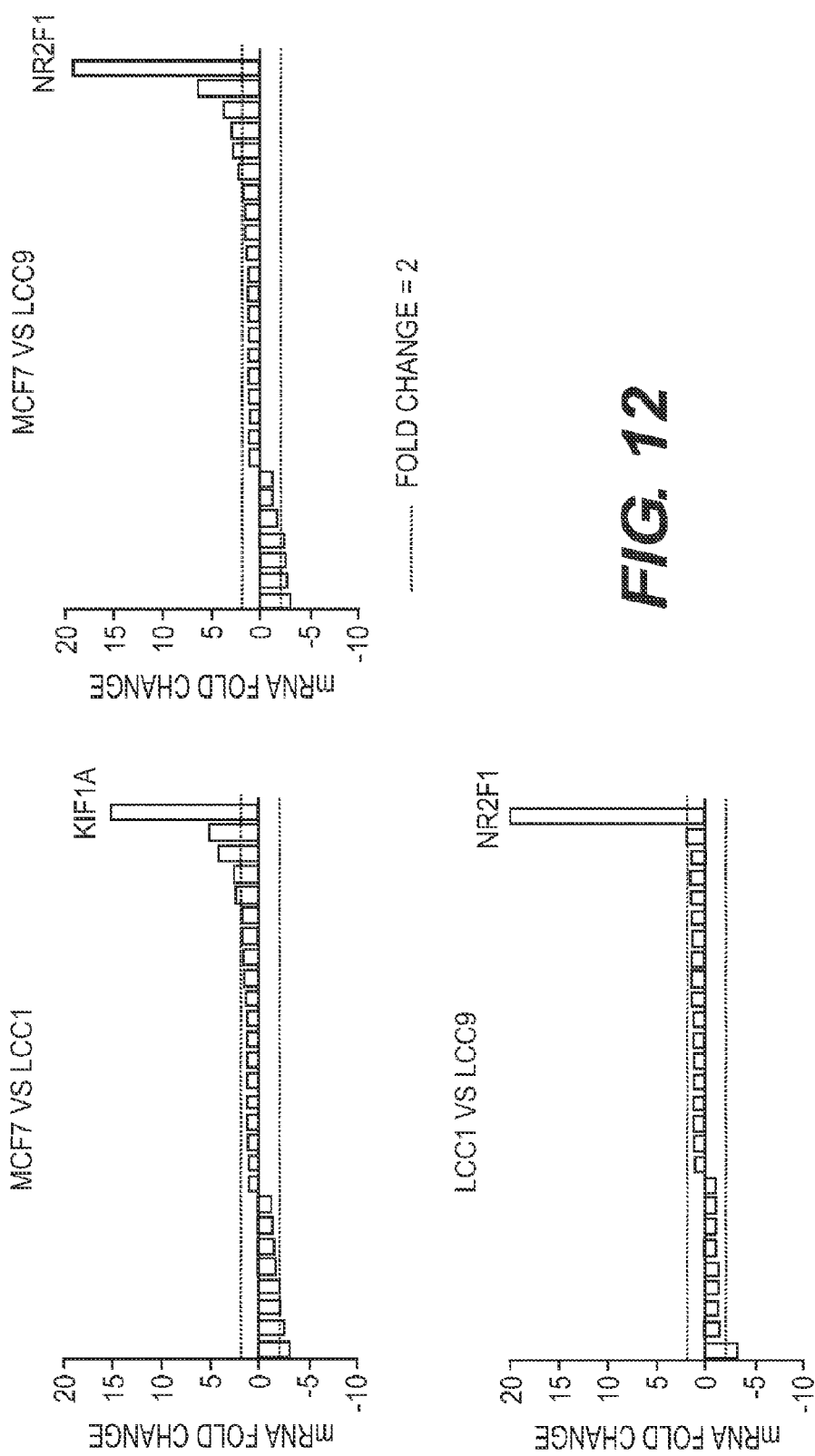
FIG. 12 depicts ER Network Survival Determinants. Gene expression does not correlate with siRNA knock-down viability or apoptosis. The 27 genes are not shared miRNA targets and do not share transcription factors.
Figure 13:
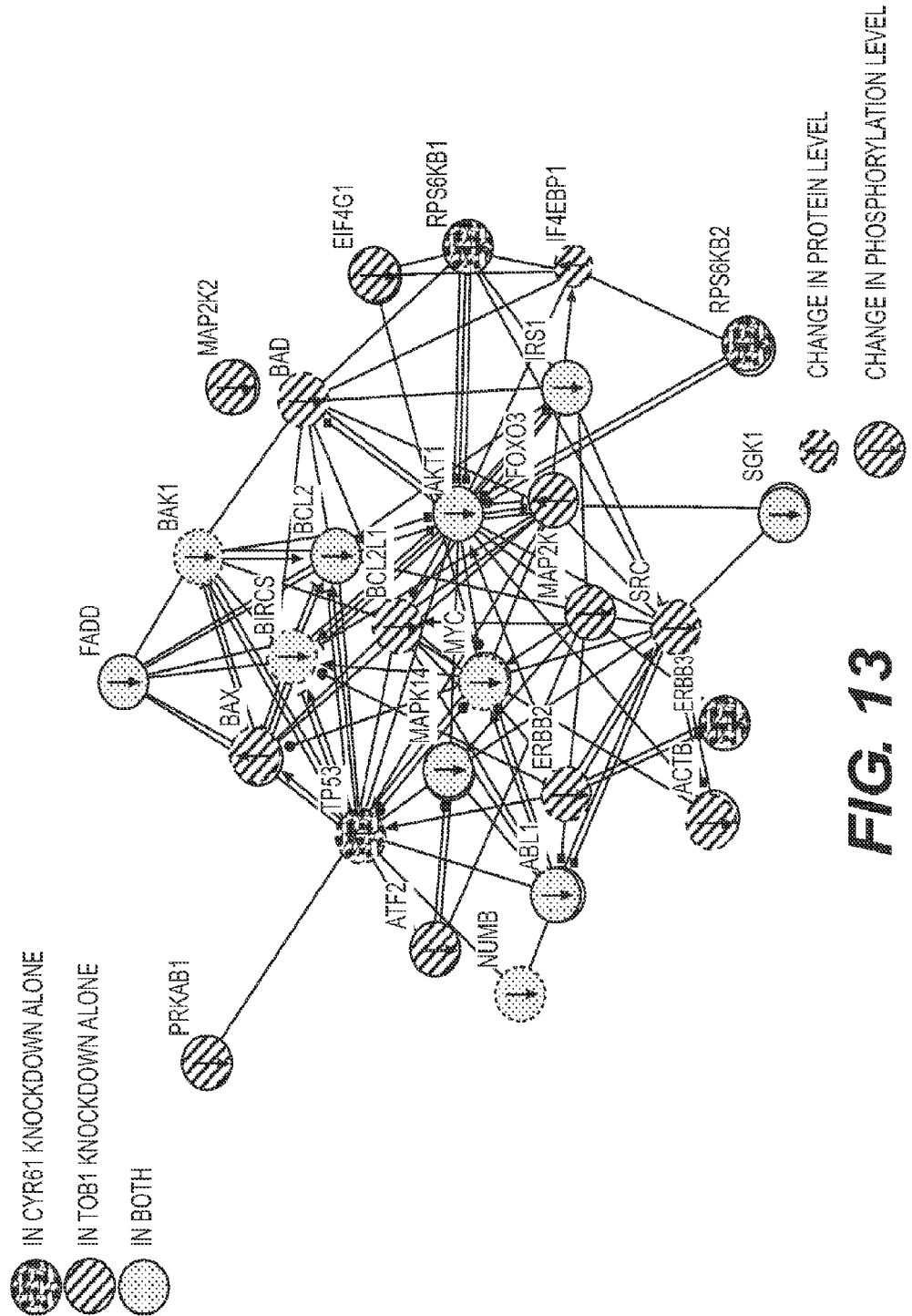
FIG. 13 depicts protein pathway activation mapping.
Figure 14:
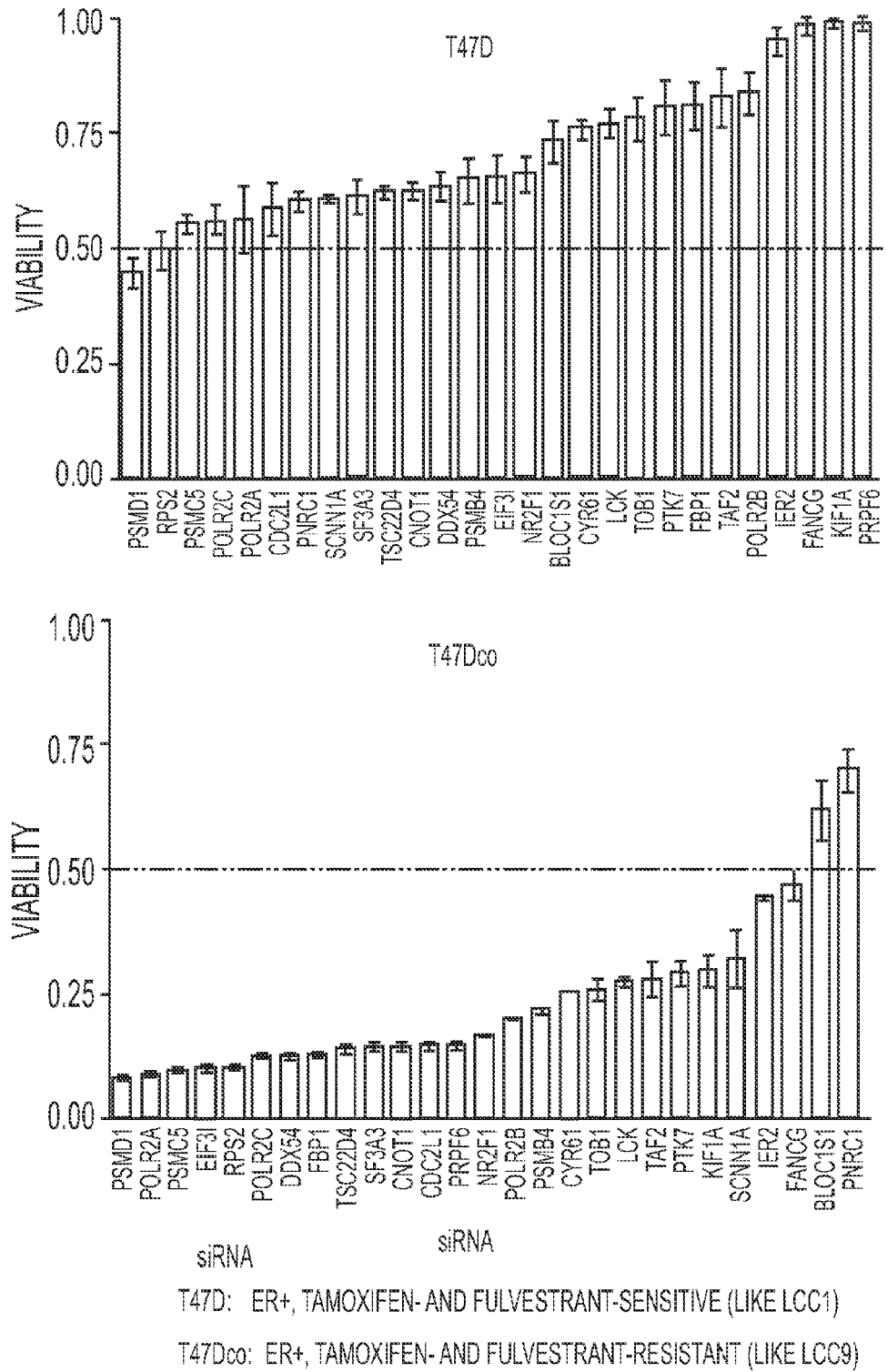
FIG. 14 depicts that the 27 gene ER survival network is not restricted to MCF7 cells.

Bortezomib is an FDA approved proteasomal inhibitor for the treatment of multiple myeloma. Three of the genes in the essential gene subset are subunits of the proteasome and when knocked-down reduce viability by more than 75% in the estrogen independent breast cancer cell lines LCC1 and LCC9. In contrast, knock-down of these genes in the parental, estrogen dependent cell line, MCF7, only reduces viability by about 25% (FIG. 8). Concentration response curves to Bortezomib for each of these cell lines shows that LCC1 and LCC9 cell lines are more sensitive to bortezomib compared to the MCF7 cell line (FIG. 8).

The inventors have discovered an network of genes that promote survival of estrogen independent cancer cells. Knockdown of one or more of these genes promotes apoptosis.

What is claimed is:

1. A method of inhibiting the growth or proliferation of an estrogen receptor positive (ER+) estrogen-independent mammary carcinoma cell, the method comprising reducing the expression or activity of CNOT1, POLR2B, PSMB4, PSMC5, and PSMD1 in the ER+ estrogen-independent mammary carcinoma cell.

2. The method of claim 1, further comprising reducing the expression or activity of TOB1 and POLR2C.

3. The method of claim 1, wherein the ER+ estrogen-independent mammary carcinoma cell is an anti-estrogen-resistant cancer cell.

* * * * *

UNITED STATES PATENT AND TRADEMARK OFFICE
CERTIFICATE OF CORRECTION

PATENT NO. : 9,677,072 B2
APPLICATION NO. : 14/344773
DATED : June 13, 2017
INVENTOR(S) : Louis M. Weiner et al.

Page 1 of 1

It is certified that error appears in the above-identified patent and that said Letters Patent is hereby corrected as shown below:

In the Specification

At Column 1, Lines 16-19, delete the following paragraph:
"Part of the work performed during development of this invention utilized U.S. Government funds under National Cancer Institute (NCI) Grant No. CA149147-01. The U.S. Government has certain rights in this invention."

And insert in its place:
--This invention was made with government support under CA149147 awarded by the National Institutes of Health. The government has certain rights in the invention.--

Signed and Sealed this
Fourth Day of February, 2025

Coke Morgan Stewart
*Acting Director of the United States Patent and Trademark Office*